United States Patent
Kim et al.

(10) Patent No.: US 8,362,470 B2
(45) Date of Patent: Jan. 29, 2013

(54) ORGANIC LIGHT EMITTING DEVICE

(75) Inventors: Young-Kook Kim, Yongin (KR);
Seok-Hwan Hwang, Yongin (KR);
Yoon-Hyun Kwak, Yongin (KR);
Hye-Jin Jung, Yongin (KR); Jong-Hyuk Lee, Yongin (KR); Jin-O Lim, Yongin (KR); Chang-Ho Lee, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 149 days.

(21) Appl. No.: 12/862,668

(22) Filed: Aug. 24, 2010

(65) Prior Publication Data
US 2011/0057175 A1  Mar. 10, 2011

(30) Foreign Application Priority Data
Sep. 4, 2009 (KR) .................. 10-2009-0083507

(51) Int. Cl.
*H01L 29/08* (2006.01)
(52) U.S. Cl. .................. 257/40; 257/E51.028
(58) Field of Classification Search .................. 257/40, 257/E51.027, E51.028
See application file for complete search history.

(56) References Cited

U.S. PATENT DOCUMENTS

| | | | |
|---|---|---|---|
| 5,645,948 A | 7/1997 | Shi et al. | |
| 6,529,541 B1 | 3/2003 | Ueki et al. | |
| 6,650,683 B2 | 11/2003 | Ueki et al. | |
| 2005/0140308 A1* | 6/2005 | Park ..................... | 315/169.3 |
| 2006/0223993 A1 | 10/2006 | Connor et al. | |
| 2006/0286483 A1 | 12/2006 | Yano et al. | |
| 2008/0220285 A1 | 9/2008 | Vestweber et al. | |
| 2009/0054652 A1 | 2/2009 | Yano et al. | |
| 2009/0159877 A1 | 6/2009 | Meng | |
| 2009/0261717 A1 | 10/2009 | Buesing et al. | |

FOREIGN PATENT DOCUMENTS

| | | |
|---|---|---|
| JP | 2005093159 A | 4/2005 |
| JP | 2008028424 A | 2/2008 |
| KR | 1020060069442 A | 6/2006 |
| KR | 1020080109000 A | 12/2008 |
| KR | 1020080114742 A | 12/2008 |
| WO | WO 2006/122630 A1 | 11/2006 |

OTHER PUBLICATIONS

European Search Report dated Dec. 17, 2010, for corresponding European Patent application 10251549.1, 10 pages.
KIPO Office action dated May 24, 2011, for Korean priority Patent application 10-2009-0083507, 5 pages.
Samsoniya, A., et. al., *Synthesis of some derivatives of indole and indoloindoles under conditions of interphase catalysis*, Chemistry of Heterocyclic Compounds, vol. 27, No. 4, Apr. 1, 1991, pp. 366-369, XP002610751.
Samsoniya, A., et al., *Bisindoles. 4. Electrophilic substitution in the IH, 6H-indolo[7,6-g]indole series*, Chemistry of Heterocyclic Compounds, vol. 15, No. 9, Sep. 1, 1979, pp. 989-994, XP002610752.

(Continued)

*Primary Examiner* — John C Ingham
(74) *Attorney, Agent, or Firm* — Christie, Parker & Hale, LLP

(57) ABSTRACT

Embodiments of the present invention are directed to a heterocyclic compound and an organic light-emitting device including the heterocyclic compound. The organic light-emitting devices using the heterocyclic compounds have high-efficiency, low driving voltage, high luminance and long lifespan.

16 Claims, 1 Drawing Sheet

OTHER PUBLICATIONS

Samsoniya, A., et al., *Bisindoles. 6. Synthesis and Investigation of Some Properties of 2-Formyl-, 3-Formyl-, and 3,8-DiFormyl-1H,6H-Indolo[7,6g]indoles*, Chemistry of Heterocyclic Compounds, vol. 16, No. 11, Nov. 1, 1980, pp. 1139-1146, XP002610753.

Samsoniya, A., et. al., *Synthesis of the IH,6H-indolo[7,6-g]indole system*, Chemistry of Heterocyclic Compounds, vol. 13, No. 9, Sep. 1, 1977, p. 1035, XP002610754.

Samsoniya, A., et. al, *Bisindoles. 38. Synthesis of some derivatives of 1H,6H-indolo[7,6-g]indole*, Chemistry of Heterocyclic Compounds, vol. 38, No. 4, Apr. 1, 2002, pp. 396-399, XP002610755.

Samsoniya, A., et. al., *Synthesis and biological activity of indoloindoles*, Pharmaceutical Chemistry Journal, vol. 25, No. 9, Sep. 1, 1991, pp. 638-642, XP002610756.

Soloducho, J., et. al., New Route to the synthesis of the Indolo[7,6-g]Indole ("Bis(Pyrrolo)naphthalene") system Starting from 1,5-Dihydroxynaphthalene, Tetrahedron Letters, vol. 40, No. 12, Jun. 15, 1999, pp. 2429-2430, XP002610757.

Dufour, F., et. al., *Carbazolo[2,1-α]carbazole Derivatives via Fischer Indole Synthesis*, Journal of Heterocyclic Chemistry, vol. 45, No. 1, Jan. 1, 2008, pp. 161-163, XP002610758.

\* cited by examiner

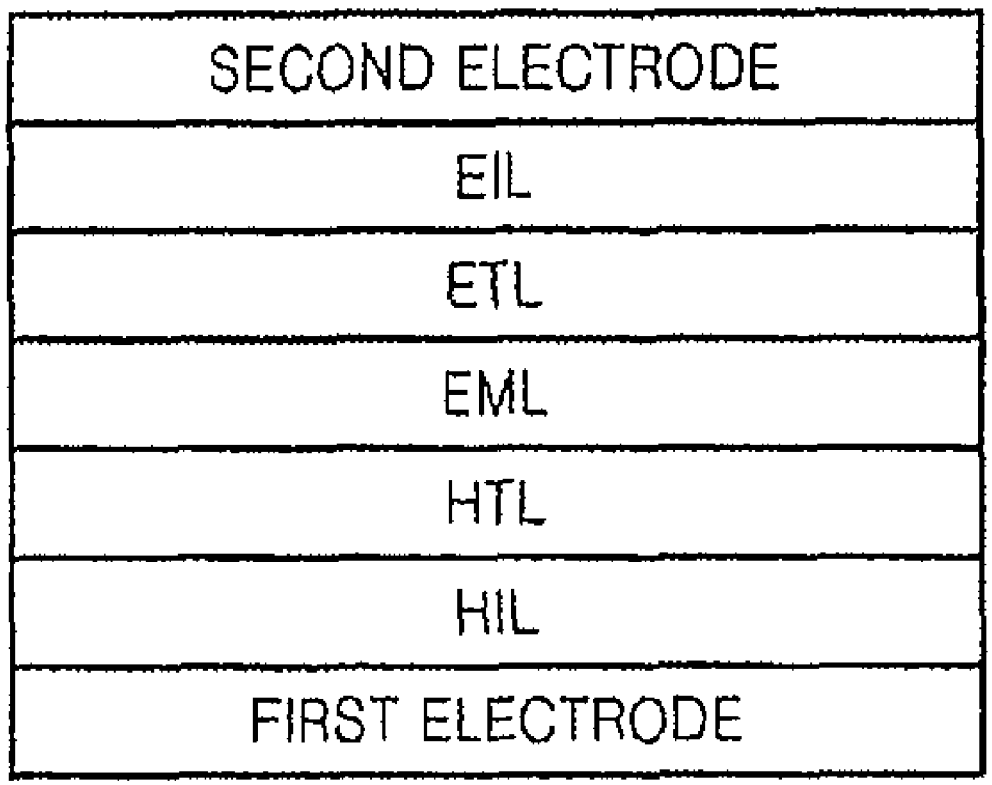

ORGANIC LIGHT EMITTING DEVICE

CROSS-REFERENCE TO RELATED PATENT APPLICATION

This application claims priority to and the benefit of Korean Patent Application No. 10-2009-0083507 filed on Sep. 4, 2009 in the Korean Intellectual Property Office, the entire content of which is incorporated herein by reference.

BACKGROUND OF THE INVENTION

1. Field of the Invention

The present invention relates to heterocyclic compounds and organic light-emitting devices including the heterocyclic compounds.

2. Description of the Related Art

Organic light-emitting devices are self-emission type display devices, and have wide viewing angles, high contrast ratios, and short response times. Due to these characteristics, organic light-emitting devices are drawing much attention.

Light-emitting devices can be roughly classified into inorganic light-emitting devices which include emission layers (EMLs) containing inorganic compounds, and organic light-emitting devices which include EMLs containing organic compounds. Organic light-emitting devices have higher luminance, lower driving voltages, and shorter response times than inorganic light-emitting devices. In addition, organic light-emitting devices produce various colors. Thus, research has been conducted into organic light-emitting devices.

Typically, an organic light-emitting device has a stack structure including an anode, a cathode and an organic emission layer between the anode and cathode. However, a hole injection layer (HIL) and/or a hole transport layer (HTL) may be further stacked between the anode and the organic emission layer, and/or an electron transport layer (ETL) may be further stacked between the organic emission layer and the cathode. In other words, an organic light-emitting device may have an anode/HTL/organic EML/cathode stack structure or an anode/HTL/organic EML/ETL/cathode stack structure.

As a material for forming the organic emission layer, phenanthrene derivatives, anthracene derivatives, and the like can be used. However, organic light-emitting devices including known light-emitting materials do not have satisfactory life span, efficiency, or power consumption characteristics, thus leaving much room for improvement.

SUMMARY OF THE INVENTION

According to embodiments of the present invention, a heterocyclic compound has improved electrical characteristics, charge transporting capabilities and light-emission capabilities.

In some embodiments of the present invention, an organic light-emitting device includes the heterocyclic compound.

In other embodiments of the present invention, a flat panel display device includes the organic light-emitting device.

According to some embodiments of the present invention, an organic light-emitting device includes at least one layer containing the heterocyclic compound, where the at least one layer is formed using a wet process.

According to embodiments of the present invention, a heterocyclic compound includes compounds represented by Formula 1 below:

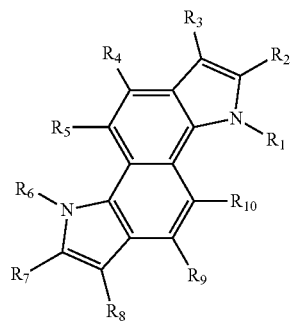

Formula 1

In Formula 1, each of $R_1$ through $R_{10}$ is independently selected from hydrogen atoms, heavy hydrogen atoms, substituted and unsubstituted $C_1$-$C_{50}$ alkyl groups, substituted and unsubstituted $C_3$-$C_{50}$ cycloalkyl groups, substituted and unsubstituted $C_1$-$C_{50}$ alkoxy groups, substituted and unsubstituted $C_5$-$C_{50}$ aryloxy groups, substituted and unsubstituted $C_5$-$C_{50}$ arylthio groups, substituted and unsubstituted $C_5$-$C_{60}$ aryl groups, amino groups substituted with at least one $R_5$-$R_{60}$ aryl group, substituted and unsubstituted $C_4$-$C_{60}$ heteroaryl groups, substituted and unsubstituted $C_6$-$C_{60}$ condensed polycyclic groups, halogen atoms, cyano groups, nitro groups, hydroxyl groups, and carboxyl groups. Neighboring substituents selected from $R_1$ through $R_{10}$ may optionally bond to each other, thereby forming an aromatic ring.

$R_1$ and $R_6$ may be the same, $R_2$ and $R_7$ may be the same, $R_3$ and $R_8$ may be the same, $R_4$ and $R_9$ may be the same, or $R_5$ and $R_{10}$ may be the same.

$R_1$ may be selected from unsubstituted monocyclic to tetracyclic aryl groups, unsubstituted $C_4$-$C_{60}$ heteroaryl groups, unsubstituted $C_5$-$C_{50}$ arylamine groups, substituted monocyclic to tetracyclic aryl groups, substituted $C_4$-$C_{60}$ heteroaryl groups, and substituted $C_5$-$C_{50}$ arylamine groups. The unsubstituted monocyclic to tetracyclic aryl groups may be selected from phenyl groups, naphthyl groups, biphenyl groups, terphenyl groups, anthracenyl groups, fluorenyl groups, carbazolyl groups, and pyrene groups. The substituted monocyclic to tetracyclic aryl groups may be selected from phenyl groups, naphthyl groups, biphenyl groups, terphenyl groups, anthracenyl groups, fluorenyl groups, carbazolyl groups, and pyrene groups substituted with at least one substituent selected from heavy hydrogen atoms, $C_1$-$C_5$ alkyl groups, $C_1$-$C_5$ alkoxy groups, cyano groups, amine groups, phenoxy groups, phenyl groups and halogen groups. The substituted $C_4$-$C_{60}$ heteroaryl groups may be selected from groups substituted with at least one substituent selected from heavy hydrogen atoms, $C_1$-$C_5$ alkyl groups, $C_1$-$C_5$ alkoxy groups, cyano groups, amine groups, phenoxy groups, phenyl groups, halogen groups and $C_5$-$C_{10}$ heteroaryl groups. The substituted $C_5$-$C_{50}$ arylamine groups may be selected from groups substituted with at least one substituent selected from heavy hydrogen atoms, $C_1$-$C_5$ alkyl groups, $C_1$-$C_5$ alkoxy groups, cyano groups, amine groups, phenoxy groups, phenyl groups and halogen groups.

In some embodiments, each of $R_2$, $R_3$, $R_7$ and $R_8$ may be independently selected from methyl groups and phenyl groups.

In some embodiments, the heterocyclic compound may include one of Compounds 3, 12, 32 and 33 below:

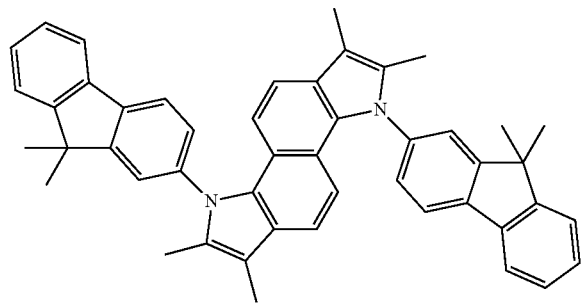

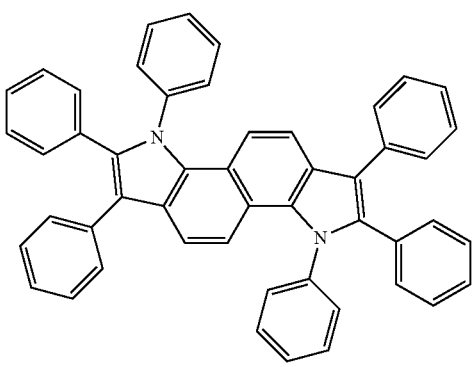

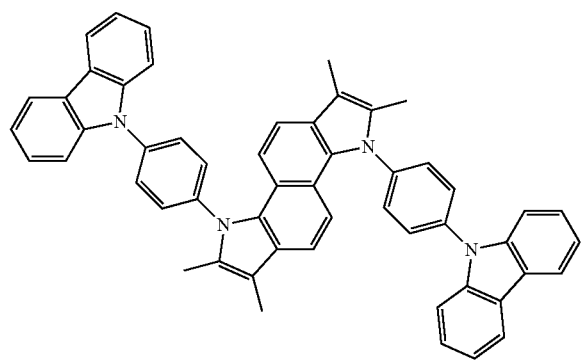

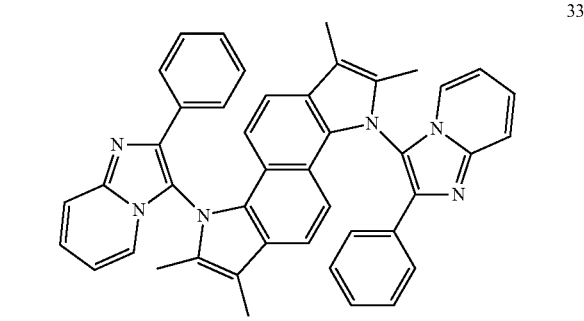

According to other embodiments of the present invention, an organic light-emitting device including a first electrode, a second electrode, and at least one organic layer between the first electrode and the second electrode. The at least one organic layer includes at least one layer including the heterocyclic compound.

The organic layer may include an electron injection layer or an electron transport layer.

The organic layer may include a single layer having both electron injection and electron transport capabilities.

The organic layer may include an emission layer.

The organic layer may include an emission layer, and the heterocylic compound may be used as a fluorescent or phosphorescent host.

The organic layer may include an emission layer, and the heterocylic compound may be used as a fluorescent dopant.

The organic layer may include an emission layer and an electron injection layer or an electron transport layer, and the emission layer may include an anthracene compound.

The organic layer may include an emission layer and an electron injection layer or an electron transport layer, and the emission layer may include an arylamine compound.

The organic layer may include an emission layer and an electron injection layer or an electron transport layer, and the emission layer may include a styryl compound.

The organic layer may include an emission layer, and an electron injection layer or an electron transport layer, and the emission layer may include a red emission layer, a green emission layer, a blue emission layer, or a white emission layer, each of which may include a phosphorescent compound.

The organic layer may include at least one layer selected from a hole injection layer, a hole transport layer, an electron blocking layer, an emission layer, a hole blocking layer, an electron transport layer, and an electron injection layer.

The organic light-emitting device may have a first electrode/hole injection layer/emission layer/second electrode structure, a first electrode/hole injection layer/hole transport layer/emission layer/electron transport layer/second electrode structure, or a first electrode/hole injection layer/hole transport layer/emission layer/electron transport layer/electron injection layer/second electrode layer structure.

According to embodiments of the present invention, a flat panel display device includes the organic light-emitting device described above, where the first electrode of the organic light-emitting device is electrically connected to a source electrode or a drain electrode of a thin-film transistor.

According to other embodiments of the present invention, an organic light-emitting device includes a first electrode, a second electrode, and an organic layer between the first electrode and the second electrode. The organic layer includes at least one layer comprising the heterocyclic compound, which layer can be formed using a wet process.

BRIEF DESCRIPTION OF THE DRAWINGS

The above and other features and advantages of the present invention will become more apparent by reference to the following detailed description when considered in conjunction with the attached drawing in which:

FIG. 1 is a schematic diagram depicting the structure of an organic light-emitting device according to an embodiment of the present invention.

DETAILED DESCRIPTION OF THE INVENTION

The present invention will now be described with reference to the accompanying drawings, in which exemplary embodiments of the invention are shown.

A heterocyclic compound according to an embodiment of the present invention is represented by Formula 1 below:

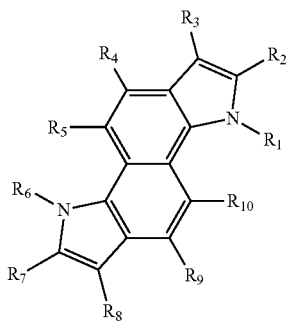

Formula 1

In Formula 1, each of $R_1$ through $R_{10}$ is independently selected from hydrogen atoms, heavy hydrogen atoms, substituted and unsubstituted $C_1$-$C_{50}$ alkyl groups, substituted and unsubstituted $C_3$-$C_{50}$ cycloalkyl groups, substituted and unsubstituted $C_1$-$C_{50}$ alkoxy groups, substituted and unsubstituted $C_5$-$C_{50}$ aryloxy groups, substituted and unsubstituted $C_5$-$C_{50}$ arylthio groups, substituted and unsubstituted $C_5$-$C_{60}$ aryl groups, amino groups substituted with at least one $R_5$-$R_{60}$ aryl group, substituted and unsubstituted $C_4$-$C_{60}$ heteroaryl groups, substituted and unsubstituted $C_6$-$C_{60}$ condensed polycyclic groups, halogen atoms, cyano groups, nitro groups, hydroxyl groups, and carboxyl groups. Neighboring substituents selected from $R_1$ through $R_{10}$ may optionally bond to each other, thereby forming an aromatic ring.

Nonlimiting examples of suitable materials for an EML or ETL (which may be included in the organic light-emitting device) include tris(8-quinolinolate)aluminum ($Alq_3$), 2,2', 2"-(1,3,5-phenylene)tris-(1-phenyl)-1H-benzimidazole (TPBI), 2-biphenyl-4-yl-5-(4-tert-butyl-phenyl)-[1,3,4]oxadiazole (PBD), perfluoronated chemical compound (PF-6P), and 2,5-bis(6'-(2',2"-bipyridyl)-1,1-dimethyl-3,4-diphenyl-silylol (PyPySPyPy). However, an organic light-emitting device manufactured using such materials does not have satisfactory lifespan, efficiency, and power consumption characteristics, leaving much room for improvement.

An organic light-emitting device manufactured using the heterocyclic compound of Formula 1 has good durability when stored or operated. In addition, due to the introduction of a substituent such as a fluorene group, molecular films may be maintained in good condition, thereby improving the characteristics of the organic light-emitting device The substituents in the heterocyclic compound of Formula 1 will now be described. In Formula 1, $R_1$ and $R_6$ may be the same, $R_2$ and $R_7$ may be the same, $R_3$ and $R_8$ may be the same, $R_4$ and $R_9$ may be the same, or $R_5$ and $R_{10}$ may be the same.

$R_1$ or $R_6$ may be selected from unsubstituted monocyclic to tetracyclic aryl groups, unsubstituted $C_4$-$C_{60}$ heteroaryl groups, unsubstituted $C_5$-$C_{50}$ arylamine groups, substituted monocyclic to tetracyclic aryl groups, substituted $C_4$-$C_{60}$ heteroaryl groups, and substituted $C_5$-$C_{50}$ arylamine groups. The unsubstituted monocyclic to tetracyclic aryl groups may be selected from phenyl groups, naphthyl groups, biphenyl groups, terphenyl groups, anthracenyl groups, fluorenyl groups, carbazolyl groups, and pyrene groups. The substituted monocyclic to tetracyclic aryl groups may be selected from phenyl groups, naphthyl groups, biphenyl groups, terphenyl groups, anthracenyl groups, fluorenyl groups, carbazolyl groups, and pyrene groups substituted with at least one substituent selected from heavy hydrogen atoms, $C_1$-$C_5$ alkyl groups, $C_1$-$C_5$ alkoxy groups, cyano groups, amine groups, phenoxy groups, phenyl groups and halogen groups. The substituted $C_4$-$C_{60}$ heteroaryl group may be selected from group substituted with at least one substituent selected from heavy hydrogen atoms, $C_1$-$C_5$ alkyl groups, $C_1$-$C_5$ alkoxy groups, cyano groups, amine groups, phenoxy groups, phenyl groups, halogen groups, and $C_5$-$C_{10}$ heteroaryl groups. The substituted $C_5$-$C_{50}$ arylamine groups may be selected from groups substituted with at least one substituent selected from heavy hydrogen atoms, $C_1$-$C_5$ alkyl groups, $C_1$-$C_5$ alkoxy groups, cyano groups, amine groups, phenoxy groups, phenyl groups and halogen groups.

In some embodiments, each of $R_2$, $R_3$, $R_7$ or $R_8$ is independently selected from methyl groups and phenyl groups.

Hereinafter, substituents described with reference to Formula 1 will now be described in detail.

The unsubstituted $C_1$-$C_{50}$ alkyl group may be linear or branched. Nonlimiting examples of the unsubstituted alkyl group include methyl groups, ethyl groups, propyl groups, isobutyl groups, sec-butyl groups, pentyl groups, iso-amyl groups, hexyl groups, heptyl groups, octyl groups, nonanyl groups, and dodecyl groups. At least one hydrogen atom of the alkyl group may be substituted with a substituent selected from heavy hydrogen atoms, halogen atoms, hydroxyl groups, nitro groups, cyano groups, amino groups, amidino groups, hydrazines, hydrazones, carboxyl groups and salts thereof, sulfonic acid groups and salts thereof, phosphoric acid groups and salts thereof, $C_1$-$C_{10}$ alkyl groups, $C_1$-$C_{10}$ alkoxy groups, $C_2$-$C_{10}$ alkenyl groups, $C_2$-$C_{10}$ alkynyl groups, $C_6$-$C_{16}$ aryl groups, and $C_4$-$C_{16}$ heteroaryl groups.

The unsubstituted $C_3$-$C_{50}$ cycloalkyl group refers to a $C_3$-$C_{50}$ cycloalkyl group. In the unsubstituted $C_3$-$C_{50}$ cycloalkyl group, one or more hydrogen atoms may be substituted with a substituent such as those described above with respect to the unsubstituted $C_1$-$C_{50}$ alkyl group.

The unsubstituted $C_1$-$C_{50}$ alkoxy group is a group having a —OA structure where A is an unsubstituted $C_1$-$C_{50}$ alkyl group as described above. Nonlimiting examples of unsubstituted $C_1$-$C_{50}$ alkoxy groups include methoxy groups, ethoxy groups, propoxy groups, isopropyloxy groups, butoxy groups, and pentoxy groups. At least one hydrogen atom of the alkoxy group may be substituted with a substituent such as those described above with respect to the $C_1$-$C_{50}$ alkyl group.

unsubstituted $C_5$-$C_{60}$ aryl group refers to a carbocyclic aromatic system containing at least one ring. At least two rings may be fused to each other or linked to each other by a single bond. As used herein, the term 'aryl' refers to an aromatic system, such as a phenyl, naphthyl, or anthracenyl system. At least one hydrogen atom in the aryl group may be substituted with a substituent such as those described above with respect to the unsubstituted $C_1$-$C_{50}$ alkyl group.

Nonlimiting examples of the substituted or unsubstituted $C_5$-$C_{60}$ aryl group include phenyl groups, $C_1$-$C_{10}$ alkylphenyl groups (for example, ethylphenyl groups), halophenyl groups (for example, o-, m-, and p-fluorophenyl groups, dichlorophenyl groups), cyanophenyl groups, dicyanophenyl groups, trifluoromethoxyphenyl groups, biphenyl groups, halobiphenyl groups, cyanobiphenyl groups, $C_1$-$C_{10}$ alkyl biphenyl groups, $C_1$-$C_{10}$ alkoxybiphenyl groups, o-, m-, and p-tolyl groups, o-, m-, and p-cumenyl groups, mesityl groups, phenoxyphenyl groups, (α,α-dimethylbenzene)phenyl groups, (N,N'-dimethyl)aminophenyl groups, (N,N'-diphenyl)aminophenyl groups, pentalenyl groups, indenyl groups, naphthyl groups, halonaphthyl groups (for example, fluoronaphthyl groups), $C_1$-$C_{10}$ alkylnaphthyl groups (for example, methylnaphthyl groups), $C_1$-$C_{10}$ alkoxynaphthyl groups (for example, methoxynaphthyl groups), cyanonaphthyl groups, anthracenyl groups, azulenyl groups, heptalenyl groups, acenaphthylenyl groups, phenalenyl groups, fluorenyl groups, anthraquinolyl groups, methylanthryl groups, phenanthryl groups, triphenylene groups, pyrenyl groups, chrysenyl groups, ethyl-chrysenyl groups, picenyl groups, perylenyl groups, chloroperylenyl groups, pentaphenyl groups, pentacenyl groups, tetraphenylenyl groups, hexaphenyl groups, hexacenyl groups, rubicenyl groups, coronenyl groups, trinaphthylenyl groups, heptaphenyl groups, heptacenyl groups, pyranthrenyl groups, and ovalenyl groups.

The unsubstituted $C_4$-$C_{60}$ heteroaryl group may include one, two or three hetero atoms selected from N, O, P and S. At least two rings may be fused to each other or linked to each other by a single bond. Nonlimiting examples of the unsubstituted $C_4$-$C_{60}$ heteroaryl group include pyrazolyl groups, imidazolyl groups, oxazolyl groups, thiazolyl groups, triazolyl groups, tetrazolyl groups, oxadiazolyl groups, pyridinyl groups, pyridazinyl groups, pyrimidinyl groups, triazinyl groups, carbazolyl groups, indolyl groups, quinolinyl groups, and isoquinolinyl groups. In the hetero aryl group, one or more hydrogen atoms may be substituted with a substituent such as those described above with respect to the unsubstituted $C_1$-$C_{50}$ alkyl group.

The unsubstituted $C_5$-$C_{50}$ aryloxy group is represented by —$OA_1$ where $A_1$ represents a $C_5$-$C_{60}$ aryl group. Nonlimiting examples of the aryloxy group include phenoxy groups. One or more hydrogen atoms in the aryl group may be substituted with a substituent such as those described above with respect to the unsubstituted $C_1$-$C_{50}$ alkyl group.

The unsubstituted $C_5$-$C_{50}$ arylthio group is represented by —$SA_1$ where $A_1$ may be a $C_5$-$C_{50}$ aryl group. Nonlimiting examples of the arylthio group may include benzenethio groups, and naphthylthio groups. One or more hydrogen atoms in the aryl group may be substituted with a substituent such as those described above with respect to the unsubstituted $C_1$-$C_{50}$ alkyl group.

The unsubstituted $C_6$-$C_{60}$ condensed polycyclic group refers to a substituent including at least two rings wherein at least one aromatic ring and/or at least one non-aromatic ring are fused to each other. The unsubstituted $C_6$-$C_{60}$ condensed polycyclic group may include one or more of the substituents described above with respect to the aryl group or heteroaryl group.

The unsubstituted $C_5$-$C_{50}$ arylamine group refers to an amine group substituted with at least one $C_5$-$C_{50}$ aryl group. The substituted $C_5$-$C_{50}$ arylamine group refers to an amine group with at least one $C_5$-$C_{50}$ aryl group, wherein the $C_5$-$C_{50}$ aryl group is substituted.

Nonlimiting examples of heterocyclic compounds represented by Formula 1 include Compounds 1 through 39 represented by the following structural formulae.

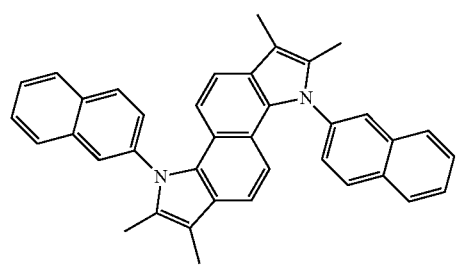

1

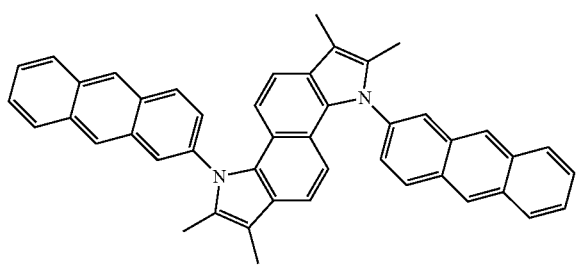

2

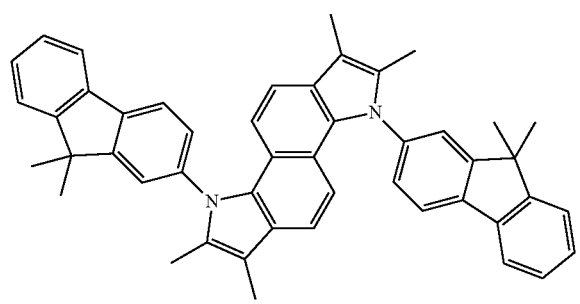

3

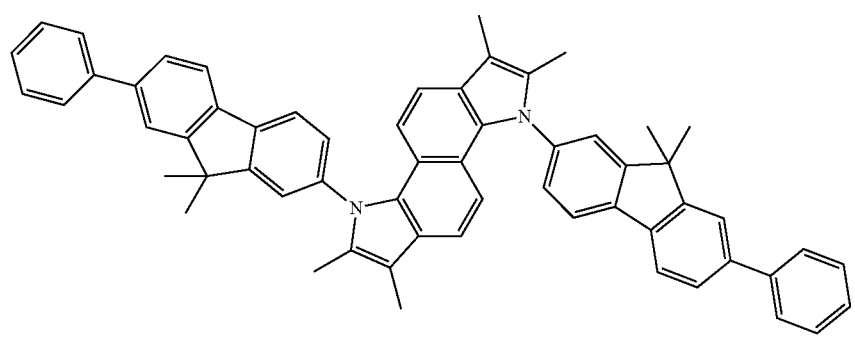

4

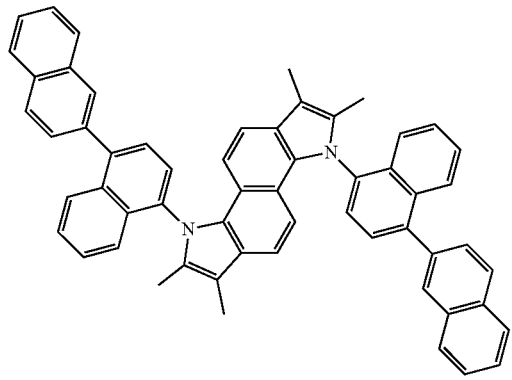
5
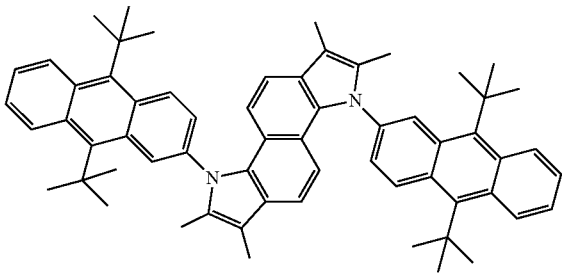
6
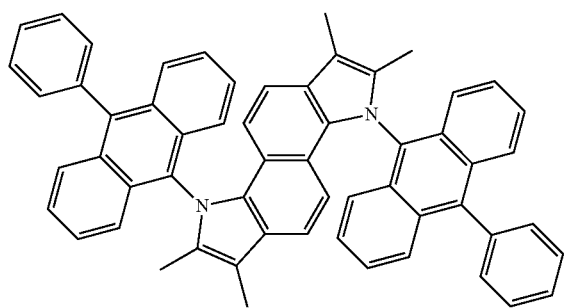
7
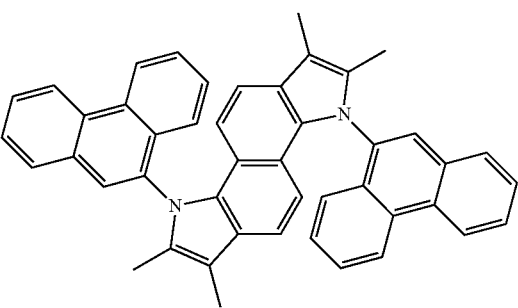
8
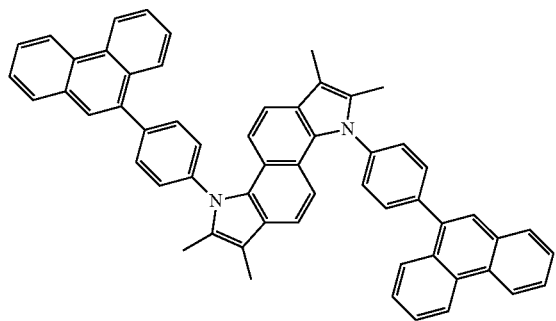
9
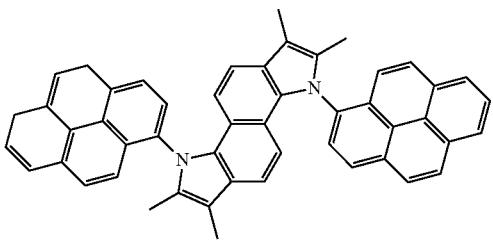
10
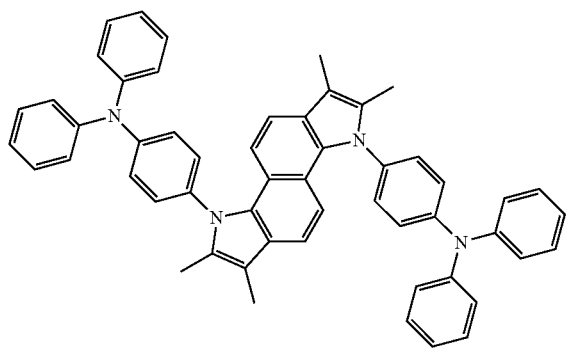
11
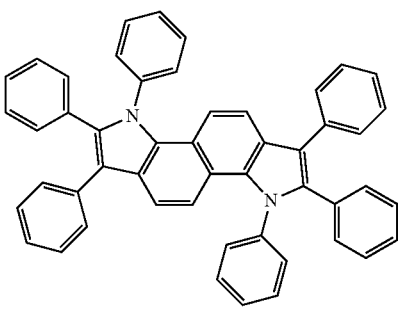
12

-continued
13
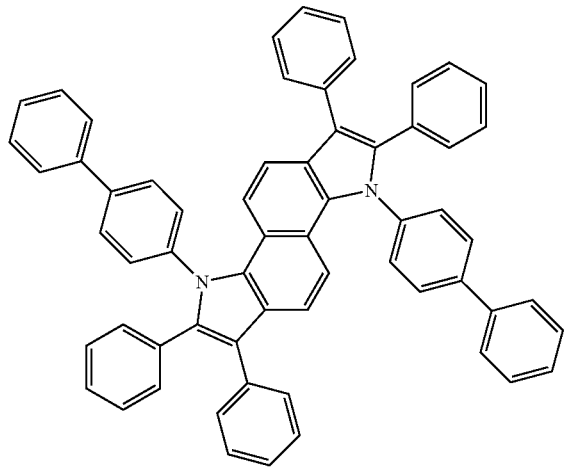
14
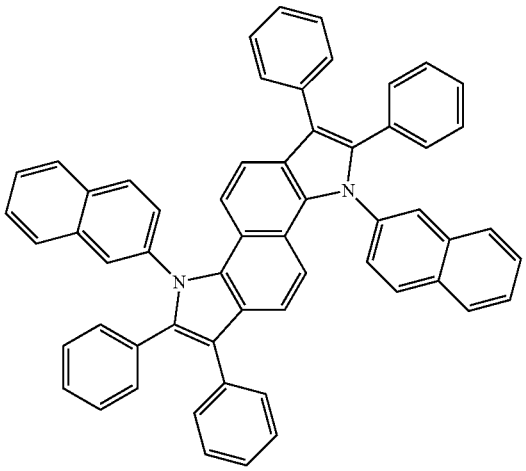
15
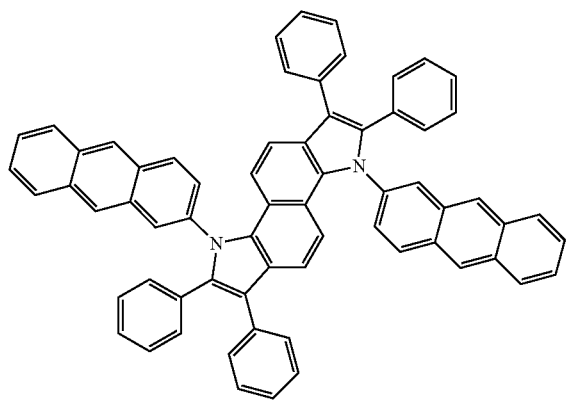
16
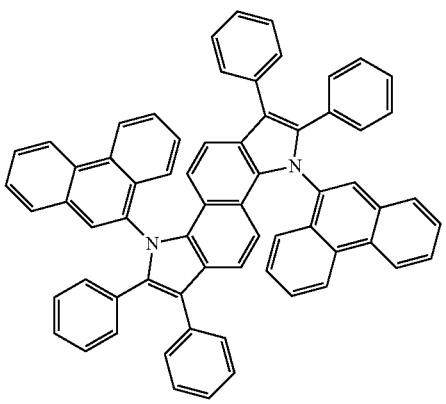
17
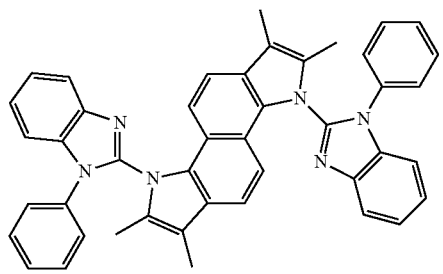
18
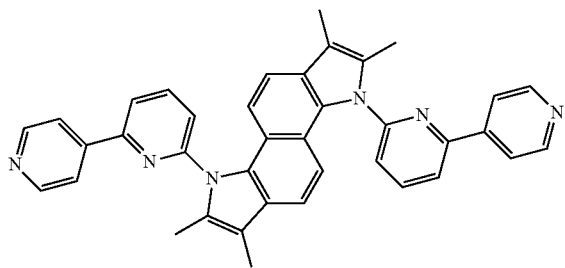
19
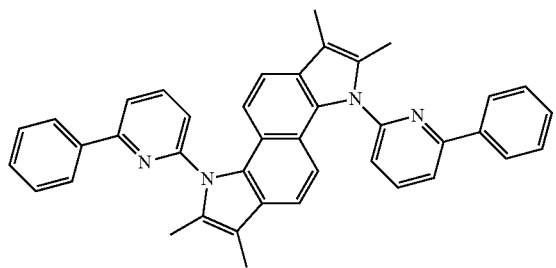
20
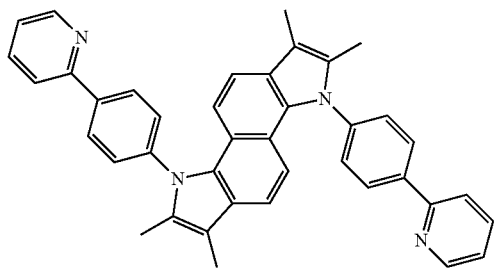

21
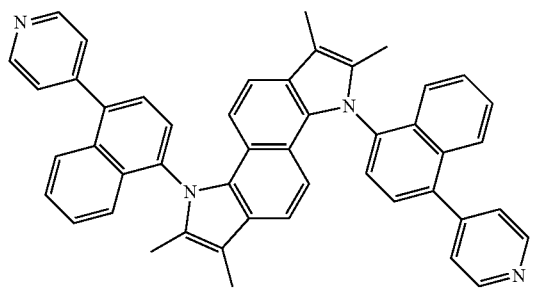
22
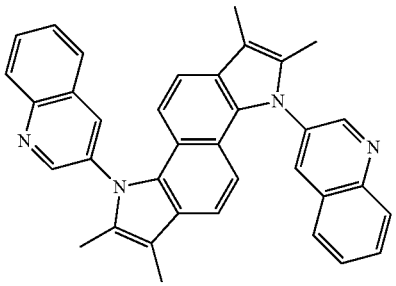
23
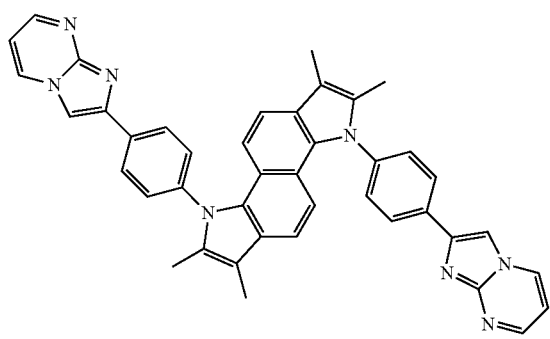
24
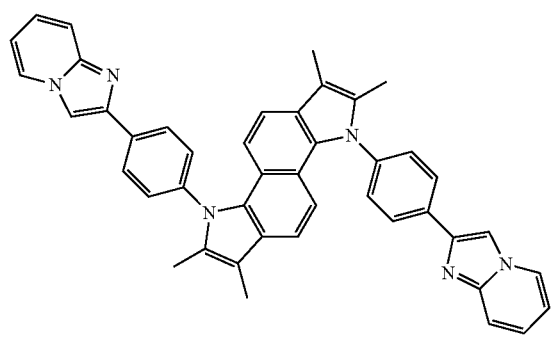
25
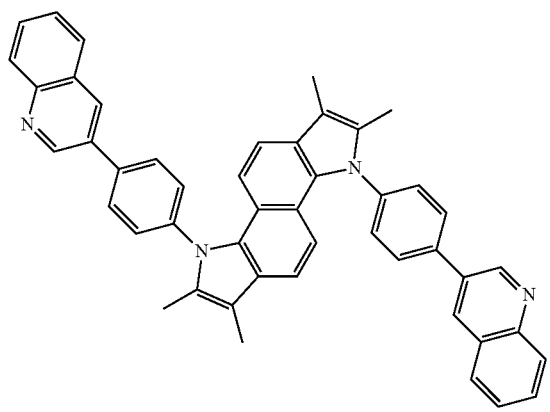
26
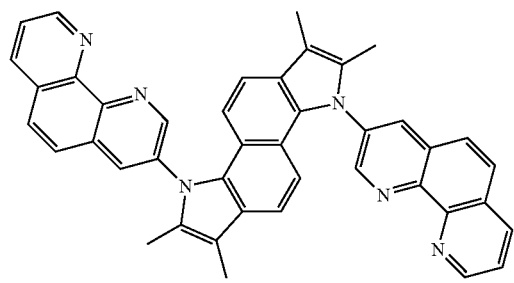
27
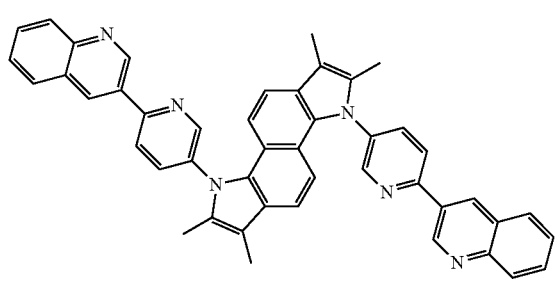
28
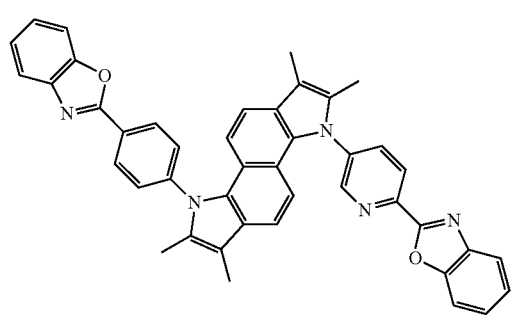

29
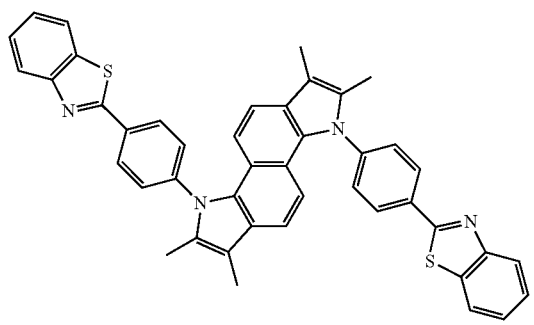
30
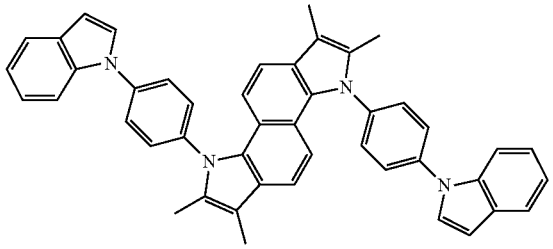
31
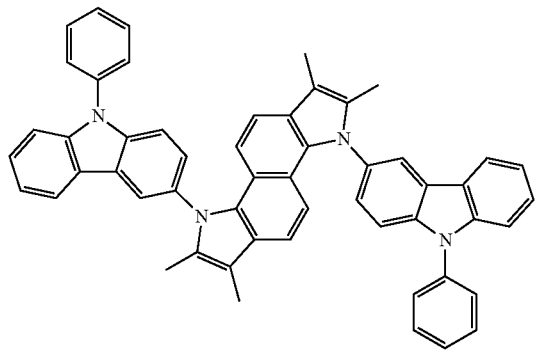
32
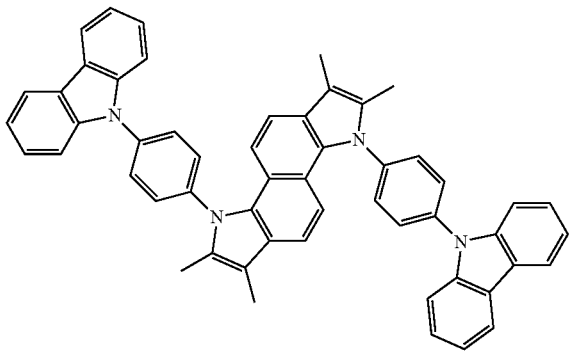
33
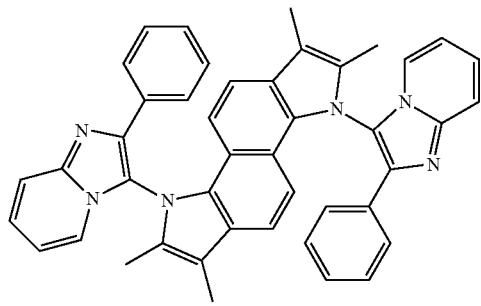
34
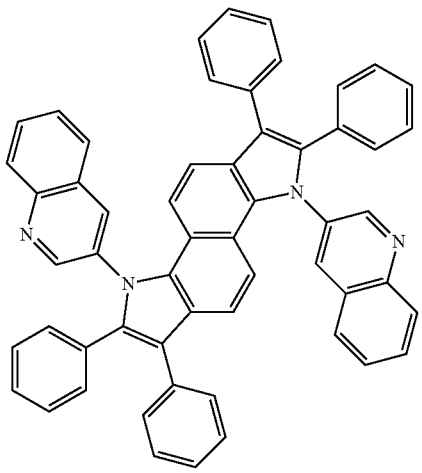
35
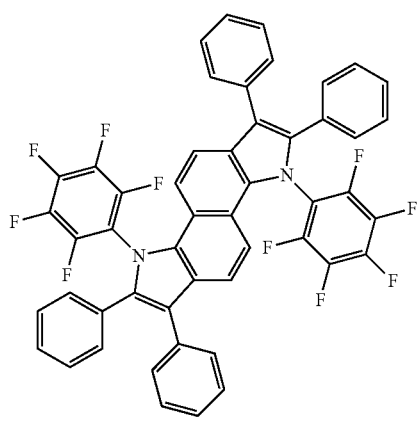
36
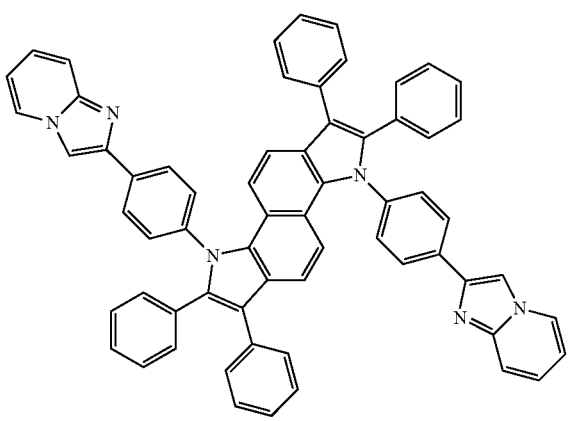

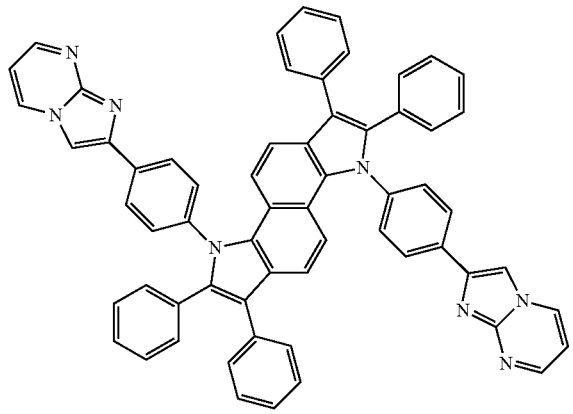

37

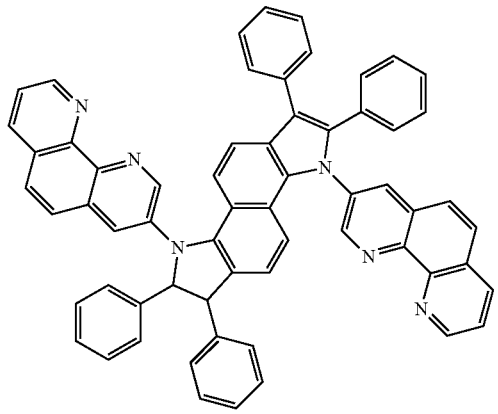

38

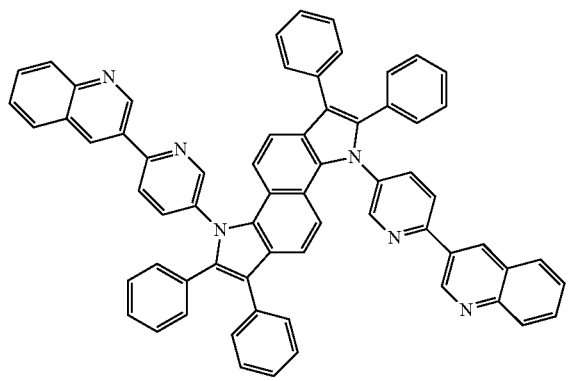

39

An organic light-emitting device according to an embodiment of the present invention includes a first electrode, a second electrode, and an organic layer between the first electrode and the second electrode, wherein the organic layer includes the heterocylic compound of Formula 1 described above.

The organic layer including the heterocyclic compound of Formula 1 may be an electron injection layer (EIL), an ETL, or a single layer having both electron injection and electron transport capabilities. Alternatively, the organic layer including the heterocyclic compound of Formula 1 may be an EML. When the organic layer including the heterocyclic compound of Formula 1 is an EML, the heterocyclic compound of Formula 1 may be used as a fluorescent host, a phosphorescent host, or a fluorescent dopant.

In the organic light-emitting device according to embodiments of the present invention, when the EML, the EIL or the ETL includes the heterocyclic compound of Formula 1, the EML may include an anthracene compound, an arylamine compound or a styryl compound. The anthracene compound, the arylamine compound or the styryl compound may be unsubstituted or substituted with a substituent such as those described above with respect to the unsubstituted $C_1$-$C_{50}$ alkyl group.

In the organic light-emitting device according to embodiments of the present invention, when the EIL or the ETL includes the heterocyclic compound of Formula 1, a red EML, a green EML, a blue EML or a white EML may include a phosphorescent compound.

The first electrode may be an anode, and the second electrode may be a cathode, but the reverse is also possible.

In the organic light-emitting device described above, the organic layer may further include at least one layer selected from a HIL, a HTL, an electron blocking layer (EBL), an EML, a hole blocking layer (HBL), an ETL and an EIL, if desired. For example, the organic light-emitting device according to embodiments of the present invention may have a first electrode/HIL/EML/second electrode structure, a first electrode/HIL/HTL/EML/ETL/second electrode structure, or a first electrode/HIL/HTL/EML/ETL/EIL/second electrode structure. Alternatively, the organic light-emitting device may have a first electrode/single layer having both hole injection and hole transport capabilities/EML/ETL/second electrode structure, or a first electrode/single layer having both hole injection and hole transport capabilities/EML/ETL/EIL/second electrode structure.

The organic light emitting device according to embodiments of the present invention may be a top-emission type organic light-emitting device or a bottom-emission type organic light-emitting device.

Hereinafter, a method of manufacturing an organic light-emitting device according to an embodiment of the present invention will be described with reference to FIG. 1. FIG. 1 illustrates the structure of an organic light-emitting device according to an embodiment of the present invention. Referring to FIG. 1, the organic light-emitting device includes a substrate, a first electrode (anode), a HIL, a HTL, an EML, an ETL, an EIL, and a second electrode (cathode).

First, a first electrode is formed on a substrate by deposition or sputtering. The first electrode may be formed of a first electrode material having a high work function. The first electrode may be an anode or a cathode. The substrate may be any substrate commonly used in organic light-emitting devices, and may be, for example, a glass substrate or a transparent plastic substrate having good mechanical strength, thermal stability, transparency, surface planarity, handling convenience, and water resistance. The first electrode material may include at least one material selected from indium tin oxide (ITO), indium zinc oxide (IZO), tin oxide ($SnO_2$), zinc oxide (ZnO), aluminum (Al), silver (Ag), and magnesium (Mg), which have good conductivity, and may form a transparent or reflective electrode.

Next, a HIL may be formed on the first electrode by various methods, for example, vacuum deposition, spin coating, casting, Langmuir-Blodgett (LB) method, or the like. When the HIL is formed using vacuum deposition, the deposition conditions may vary according to the compound used to form the HIL, and the desired structural and thermal characteristics of the HIL to be formed. For example, the deposition conditions may include a deposition temperature of about 100 to about 500° C., a vacuum pressure of about $10^{-8}$ to about $10^{-3}$ torr, and a deposition rate of about 0.01 to about 100 Å/sec.

When the HIL is formed using spin coating, the coating conditions may vary according to the compound used to form the HIL, and the structural and thermal properties of the HIL to be formed. For example, the coating conditions may include a coating speed of about 2000 rpm to about 5000 rpm, and a thermal treatment temperature of about 80° C. to about 200° C., wherein the thermal treatment removes the solvent after the coating.

The HIL may be formed of any material that is commonly used to form a HIL. Nonlimiting examples of HIL materials include phthalocyanine compound such as copperphthalocyanine, 4,4',4"-tris(3-methylphenylphenylamino) triphenylamine (m-MTDATA), N,N'-di(1-naphthyl)-N,N'-diphenyl-benzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline/poly(4-styrenesulfonate (PANI/PSS).

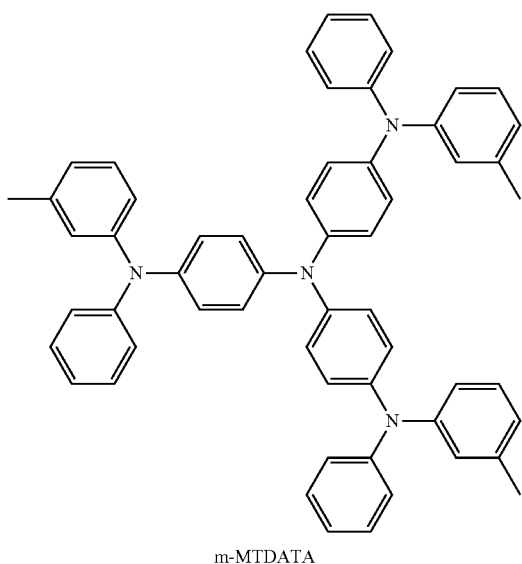

m-MTDATA

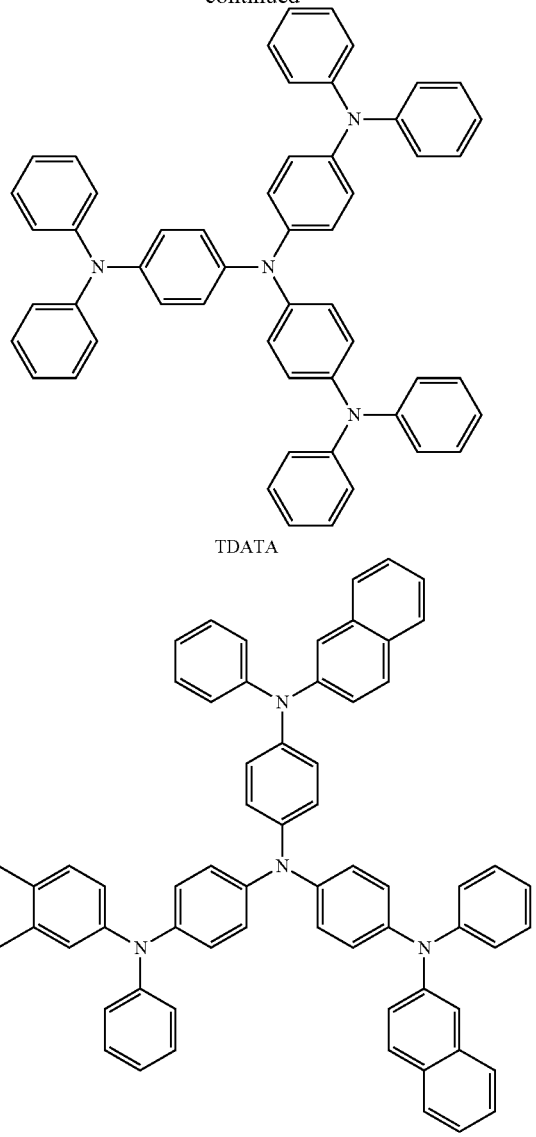

TDATA

2-TNATA

The HIL may have a thickness of about 100 Å to about 10000 Å. In some embodiments, for example, the HIL has a thickness of about 100 Å to about 1000 Å. When the HIL has a thickness within these ranges, the HIL has good hole injection characteristics without increasing driving voltage.

Next, a HTL may be formed on the HIL by various methods, for example vacuum deposition, spin coating, casting, LB method, or the like. When the HTL is formed using vacuum deposition or spin coating, the deposition or coating conditions may be similar to those used to form the HIL, although the deposition or coating conditions may vary according to the material that is used to form the HTL.

The HTL may include a known HTL material. Nonlimiting examples of HTL materials include carbazole derivatives such as N-phenylcarbazole or polyvinylcarbazole, and amine derivatives having an aromatic condensed ring such as NPB, or N,N'-bis(3-methylphenyl)-N,N'-diphenyl-[1,1-biphenyl]-4,4'-diamine (TPD). Among these materials, TCTA not only transports holes but also inhibits excitons from being diffused from the EML.

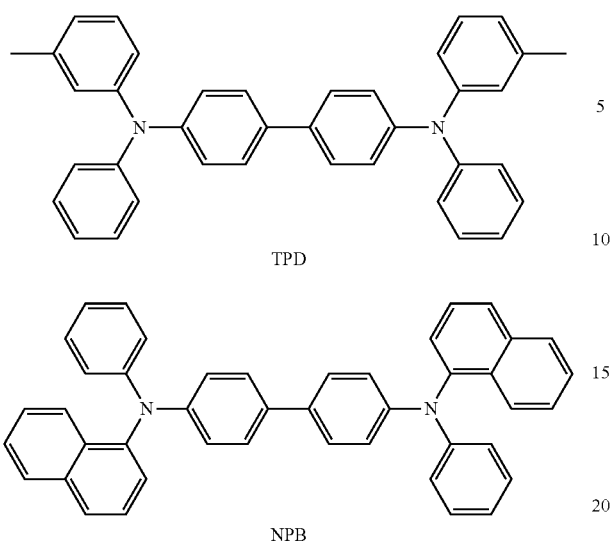

TPD

NPB

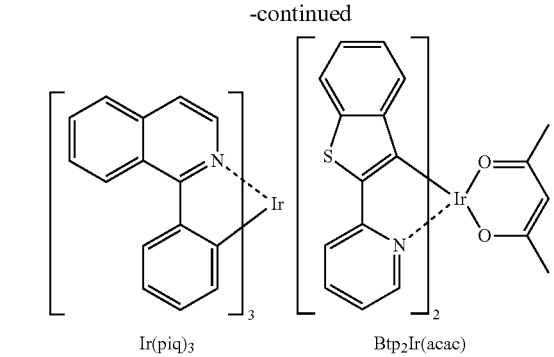

Ir(piq)₃        Btp₂Ir(acac)

Nonlimiting examples of green dopants include Ir(ppy)₃ (where "ppy" denotes phenylpyridine), Ir(ppy)₂(acac), Ir(m-pyp)₃, and C545T.

The HTL may have a thickness of about 50 Å to about 1000 Å. In some embodiments, for example, the HTL has a thickness of 100 Å to about 600 Å. When the HTL has a thickness within these ranges, the HTL has good hole transport characteristics without substantially increasing driving voltage.

Next, an EML may be formed on the HTL by various methods, for example, vacuum deposition, spin coating, casting, LB method, or the like. When the EML is formed using vacuum deposition or spin coating, the deposition or coating conditions may be similar to those used to form the HIL, although the deposition and coating conditions may vary according to the material that is used to form the EML.

The EML may include the heterocyclic compound of Formula 1 described above. In particular, the heterocyclic compound of Formula 1 may be used as a host or a dopant. The EML may include a variety of known light-emitting materials, in addition to the heterocyclic compound of Formula 1. Alternatively, the EML may also include a known host and dopant. The dopant used to form the EML may include either a fluorescent dopant or a phosphorescent dopant.

Nonlimiting examples of the host include Alq₃, 4,4'-N,N'-dicarbazole-biphenyl (CPB), 9,10-di(naphthalene-2-yl)anthracene (ADN), and distyrylarylene (DSA).

Nonlimiting examples of red dopants include platinum(II) octaethylporphyrin (PtOEP), Ir(piq)₃, Btp₂Ir(acac), and DCJTB.

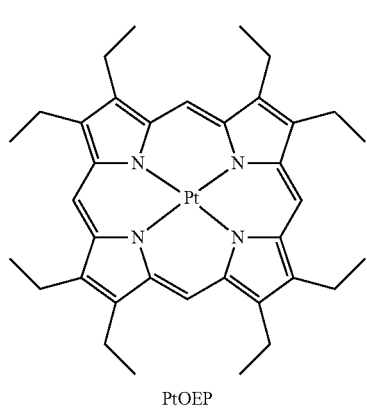

PtOEP

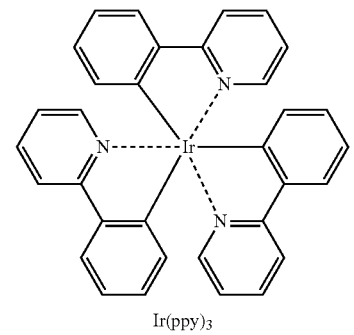

Ir(ppy)₃

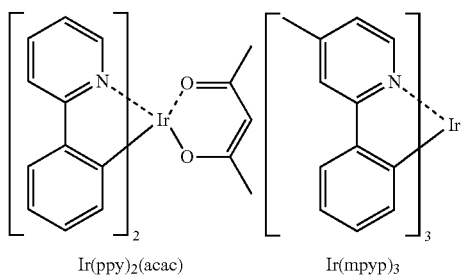

Ir(ppy)₂(acac)        Ir(mpyp)₃

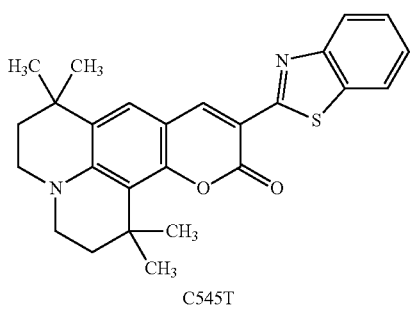

C545T

Nonlimiting examples of blue dopants include F₂Irpic, (F₂ppy)₂Ir(tmd), Ir(dfppz)₃, ter-fluorene, 4,4'-bis(4-diphenylaminostyryl)biphenyl (DPAVBi), and 2,5,8,11-tetra-t-butyl pherylene (TBP).

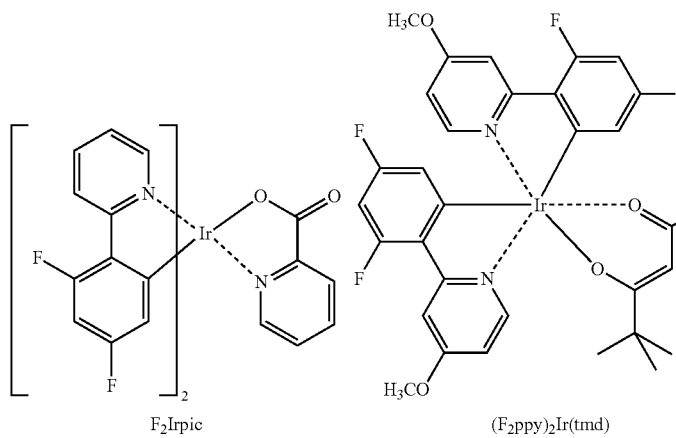

F₂Irpic  (F₂ppy)₂Ir(tmd)  Ir(dfppz)₃

DPAVBi

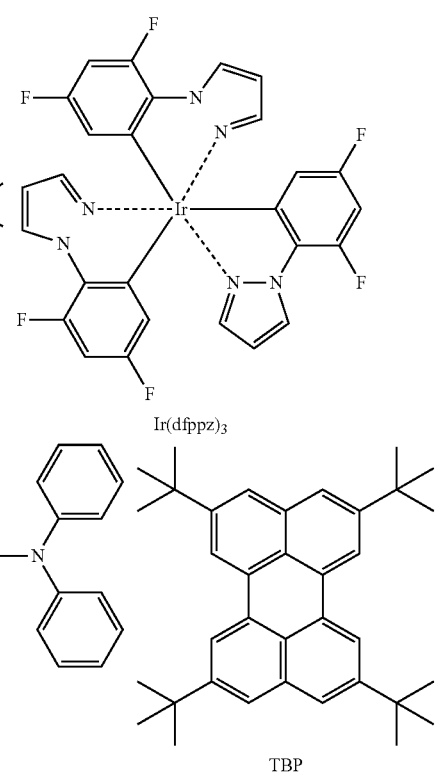

TBP

TAZ

BAlq

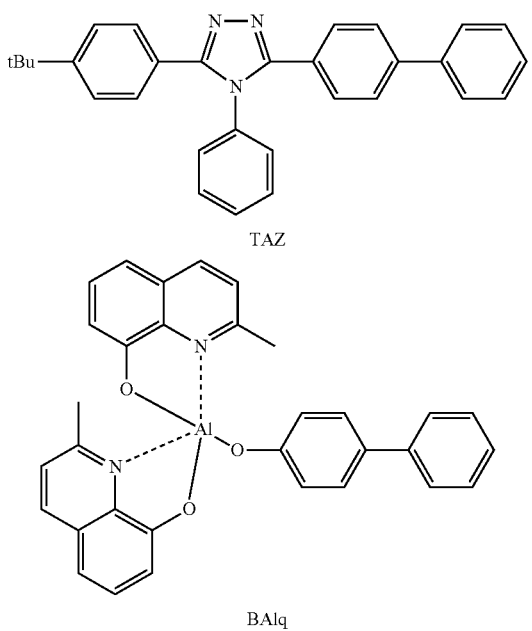

The amount of the dopant may be about 0.1 to about 20 parts by weight based on 100 parts by weight of the EML material (i.e., the total weight of the host and the dopant). In some embodiments, the amount of the dopant may be about 0.5 to about 12 parts by weight based on 100 parts by weight of the EML material. When the content of the dopant is within these ranges, concentration quenching may be substantially prevented.

The EML may have a thickness of about 100 Å to about 1000 Å. In some embodiments, for example, the EML has a thickness of about 200 Å to about 600 Å0. When the EML has a thickness within these ranges, the EML has good light-emitting characteristics without substantially increasing driving voltage.

When the EML includes a phosphorescent dopant, a HBL (not shown in FIG. 1) may be formed on the EML to prevent diffusion of triplet excitons or holes into the ETL. The HBL may be formed of any material commonly used to form a HBL, without limitation. Nonlimiting examples of HBL materials include oxadiazole derivatives, triazole derivatives, phenanthroline derivatives, Balq, and BCP.

The HBL may have a thickness of about 50 Å to about 1000 Å. In some embodiments, for example, the HBL has a thickness of about 100 Å to about 300 Å. When the thickness of the HBL is within these ranges, the HBL may have good hole blocking capability without substantially increasing driving voltage.

Next, an ETL is formed on the EML (or HBL) by various methods, for example, vacuum deposition, spin coating, casting, or the like. When the ETL is formed using vacuum deposition or spin coating, the deposition or coating conditions may be similar to those used to form the HIL, although the deposition and coating conditions may vary according to the material that is used to form the ETL.

The ETL material may include the heterocyclic compound of Formula 1 described above. Alternatively, the ETL may be formed of any known material. Nonlimiting examples of ETL materials include quinoline derivatives, such as $Alq_3$, TAZ, or Balq.

The ETL may have a thickness of about 100 Å to about 1000 Å. In some embodiments, for example, the ETL has a thickness of about 100 Å to about 500 Å. When the ETL has a thickness within these ranges, the ETL may have good electron transport characteristics without substantially increasing driving voltage.

In addition, an EIL, which facilitates injection of electrons from the cathode, may be formed on the ETL.

The EIL material may include the heterocyclic compound of Formula 1 described above. Alternatively, known EIL materials, such as LiF, NaCl, CsF, $Li_2O$, or BaO, may be used to form the EIL. The deposition or coating conditions used to form the EIL may be similar to those used to form the HIL, although the deposition and coating conditions may vary according to the material that is used to form the EIL.

The EIL may have a thickness of about 1 Å to 100 Å. In some embodiments, for example, the EIL has a thickness of about 5 Å to about 90 Å. When the EIL has a thickness within these ranges, the EIL may have good electron injection characteristics without substantially increasing driving voltage.

Finally, a second electrode may be formed on the EIL by, for example, vacuum deposition, sputtering, or the like. The second electrode may be a cathode or an anode. A second electrode material may include a metal, an alloy, an electrically conductive compound, or mixtures thereof, all of which have a low work function. Nonlimiting examples of second electrode materials include lithium (Li), magnesium (Mg), aluminum (Al), aluminum-lithium (Al—Li), calcium (Ca), magnesium-indium (Mg—In), and magnesium-silver (Mg—Ag). In addition, in order to manufacture a top-emission type organic light-emitting device, a transparent cathode formed of a transparent material such as ITO or IZO may be used as the second electrode.

The organic light-emitting device according to embodiments of the present invention may be included in various types of flat panel display devices, such as passive matrix organic light-emitting display devices or active matrix organic light-emitting display devices. When the organic light-emitting device is included in an active matrix organic light-emitting display device including a thin-film transistor, the first electrode formed on the substrate may function as a pixel electrode, and is electrically connected to a source electrode or a drain electrode of the thin-film transistor. Moreover, the organic light-emitting device may also be included in flat panel display devices having double-sided screens.

According to embodiments of the present invention, at least one layer of the organic light-emitting device may be formed of the heterocyclic compound of Formula 1 and may be applied by a deposition method or a wet method of coating a solution of the heterocyclic compound of Formula 1.

The following examples are presented for illustrative purposes only, an do not limit the scope of the present invention.

SYNTHESIS EXAMPLES

Synthesis Example 1

Synthesis of Compound 3

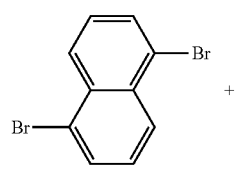

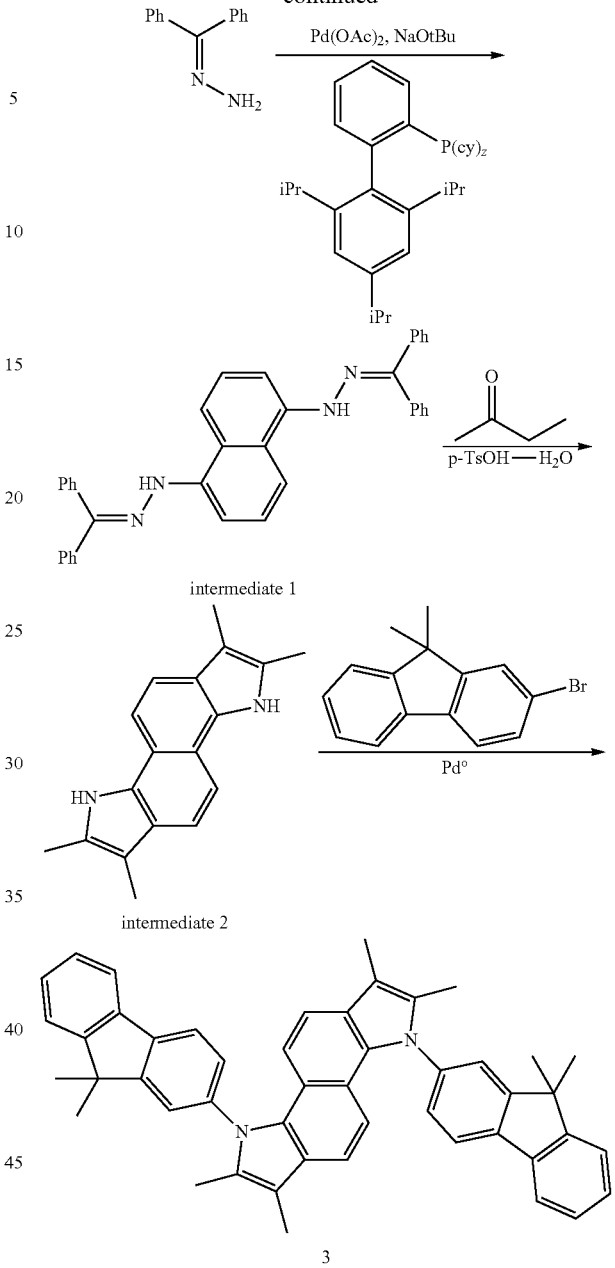

Synthesis of Intermediate 1

8.57 g (30 mmol) of 1,5-dibromonaphthalene, 7.1 g (36 mmol) of benzophenone hydrazone, 4.3 g (45 mmol) of t-BuONa, 0.13 g (0.6 mmol) of $Pd(OAc)_2$, and 0.29 g (0.6 mmol) of 2-dicyclohexylphosphino-2',4',6'-triisopropylbiphenyl were dissolved in 80 mL of toluene, and then the mixture was stirred at 90° C. for 3 hours. The mixture was cooled to room temperature, and distilled water was added thereto. Then, the mixture was subjected to extraction twice with 100 mL of diethylether and once with 100 mL of dichloromethane. An organic layer was collected and dried using magnesium sulfate, followed by filtration. The solvent was evaporated, and the residue was separated and purified using silica gel column chromatography to obtain 13.9 g (yield:

90%) of Intermediate 1. This compound was identified using high-resolution mass spectra (HR-MS). $C_{36}H_{28}N_4$ calc.: 516.2314. found: 516.2315

Synthesis of Intermediate 2

10.3 g (20 mmol) of Intermediate 1, 7.6 g (40 mmol) of p-toluenesulfonic acid monohydrate, and 10 mL of methylethyl ketone were dissolved in 50 mL of ethanol, and the mixture was stirred at 110° C. for 24 hours. The mixture was cooled to room temperature, and distilled water was added thereto. Then, the mixture was subjected to extraction twice with 100 mL of diethylether and twice with 100 mL of dichloromethane. An organic layer was collected and dried using magnesium sulfate, followed by filtration. The solvent was evaporated, and the residue was separated and purified using silica gel column chromatography to obtain 3.78 g (yield: 72%) of Intermediate 2. This compound was identified using HR-MS. $C_{18}H_{18}N_2$ calc.: 262.1470. found: 262.1472

Synthesis of Compound 3

2.62 g (10 mmol) of Intermediate 2, 3.29 g (12 mmol) of 9,9'-dimethyl-2-bromofluorene, 2.9 g (30 mmol) of t-BuONa, 366 mg (0.4 mmol) of $Pd_2(dba)_3$, and 80 mg (0.4 mmol) of $P(t-Bu)_3$ were dissolved in 60 ml of toluene, and then the mixture was stirred at 90° C. for 3 hours. After the reaction was completed, the mixture was cooled to room temperature and subjected to extraction three times with distilled water and 50 ml of diethylether. An organic layer was collected and dried using magnesium sulfate to evaporate the solvent. The residue was separated and purified using silica gel column chromatography to obtain 4.53 g (yield: 70%) of Compound 3. This compound was identified using HR-MS and nuclear magnetic resonance spectrometry (NMR). $C_{48}H_{42}N_2$ calc.: 646.3348. found: 646.3352; $^1H$ NMR ($CDCl_3$, 400 MHz) δ (ppm) 7.82 (m, 4H), 7.76 (d, 2H), 7.57 (d, 2H), 7.53 (d, 2H), 7.23 (t, 2H), 6.96 (t, 2H), 6.36 (d, 2H), 6.00 (dd, 2H), 2.94 (s, 6H), 2.22 (s, 6H), 1.85 (s, 12H)

Synthesis Example 2

Synthesis of Compound 12

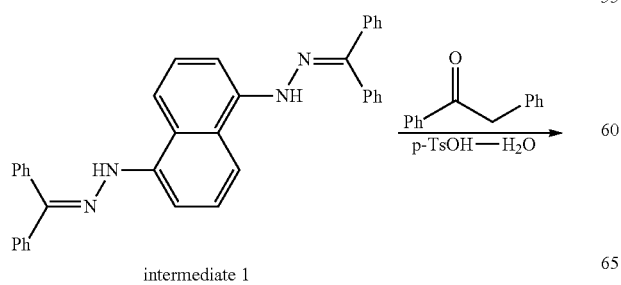

intermediate 1

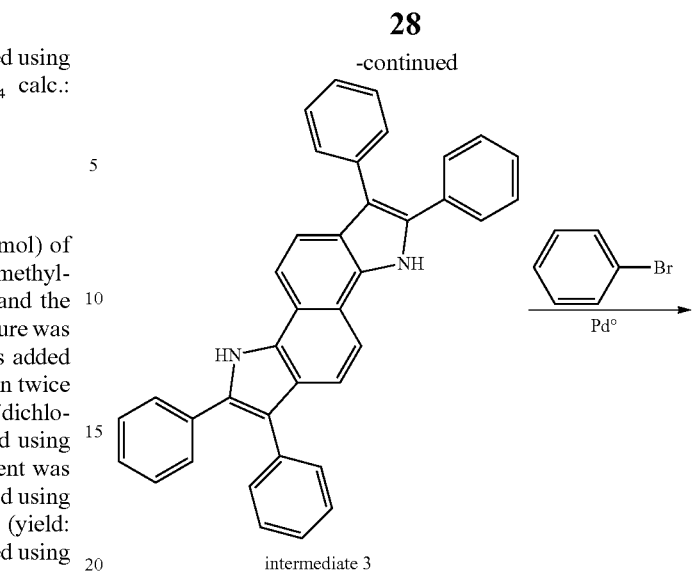

intermediate 3

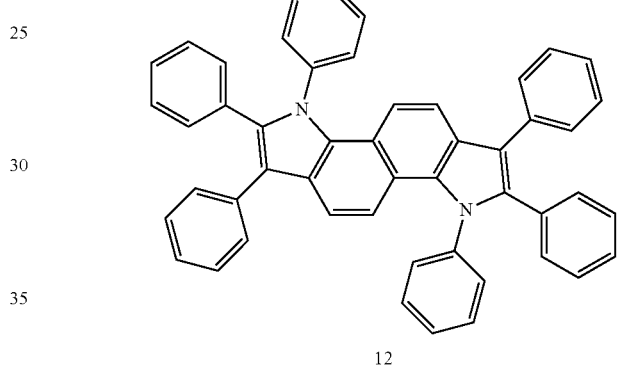

12

Synthesis of Intermediate 3

10.3 g of (20 mmol) of Intermediate 1, 7.6 g (40 mmol) of p-toluenesulfonic acid monohydrate, 15.70 g (80 mmol) of benzylphenylketone were dissolved in 80 mL of ethanol and 80 mL of toluene, and the mixture was stirred at 110° C. for 24 hours. The mixture was cooled to room temperature, and distilled water was added thereto. Then, the mixture was subjected to extraction twice with 100 mL of diethylether and once with 100 mL of dichloromethane. An organic layer was collected and dried using magnesium sulfate, followed by filtration. The solvent was evaporated, and the residue was separated and purified using silica gel column chromatography to obtain 3.11 g (yield: 61%) of Intermediate 3. This compound was identified using HR-MS. $C_{38}H_2N_2$ calc.: 510.2096. found: 510.2099

Synthesis of Compound 12

Compound 12 was synthesized with a yield of 75% in the same manner as Compound 3, except that bromobenzene was used instead of 9,9'-dimethyl-2-bromofluorene. This compound was identified using HR-MS. $C_{50}H_{34}N_2$ calc.:

662.2722. found: 662.2723; $^1$H NMR (CDCl$_3$, 400 MHz) δ (ppm) 8.37 (d, 2H), 7.99 (d, 2H), 7.57-7.25 (m, 26H), 7.05 (dd, 4H)

Synthesis Example 3

Synthesis of Compound 32

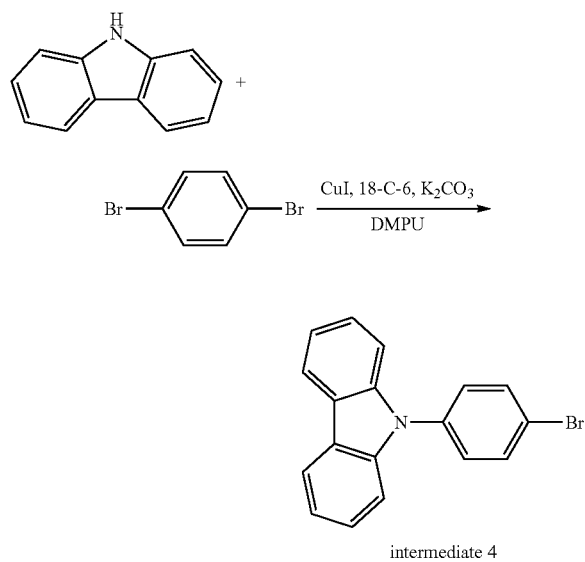

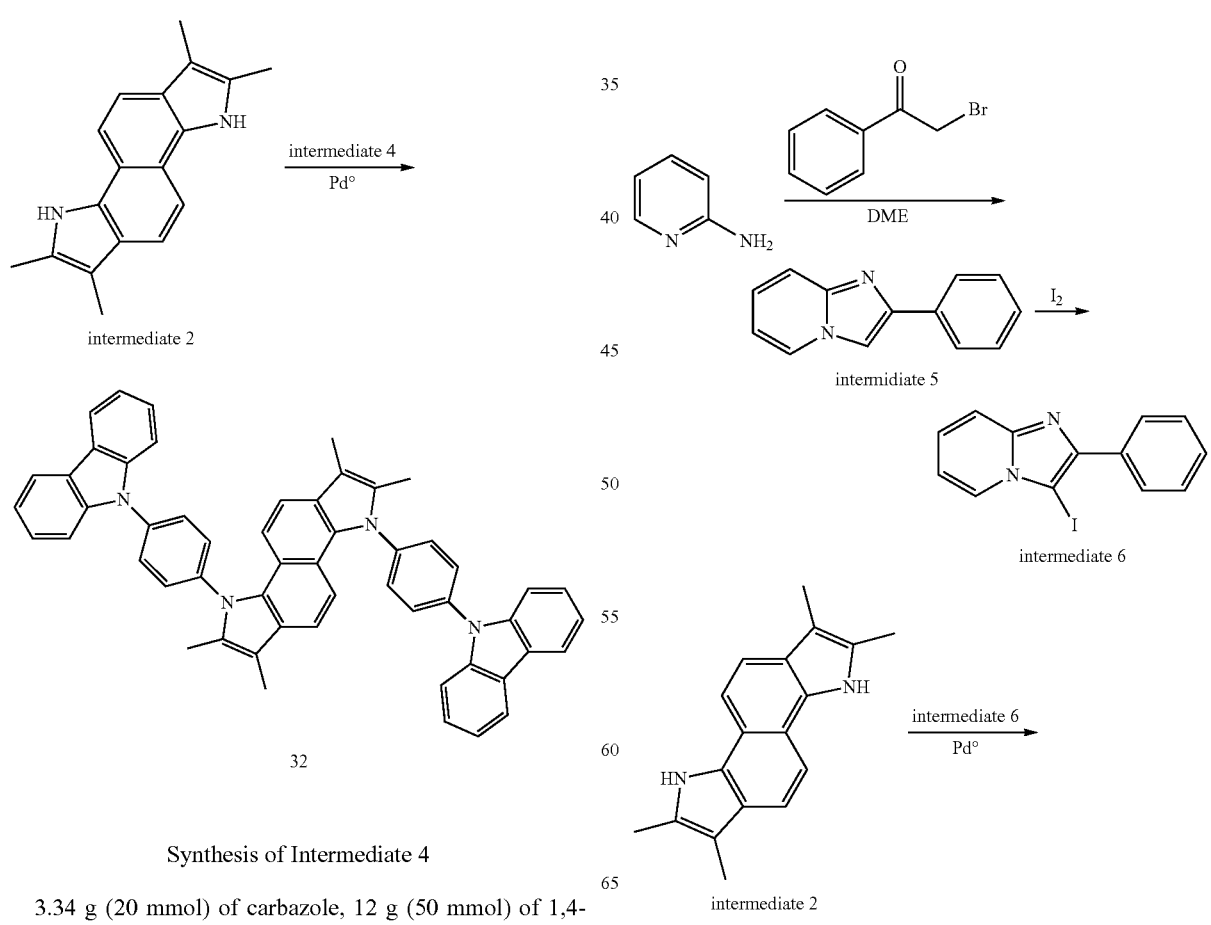

Synthesis of Intermediate 4

3.34 g (20 mmol) of carbazole, 12 g (50 mmol) of 1,4-dibromobenzene, 760 mg (4 mmol) of CuI, 11 g (80 mmol) of K$_2$CO$_3$, and 100 mg (0.4 mmol) of 18-Crown-6 were dissolved in 50 mL of 1,3-dimethyl-3,4,5,6-tetrahydro-(1H)-pyrimidinone (DMPU), and the mixture was heated at 170° C. for 8 hours. The mixture was cooled to room temperature, and filtered to obtain a solid material. A small amount of ammonia water was added to the filtrate, and the resultant was washed three times with 100 mL of diethylether. The washed diethyl ether layer was dried with MgSO$_4$ and dried under a reduced pressure to obtain a crude product. The crude product was separated and purified using silica gel column chromatography to obtain 4.83 g (yield: 75%) of solid Intermediate 4. This compound was identified using HR-MS. C$_{18}$H$_{12}$BrN calc.: 321.0153. found: 321.0151

Synthesis of Compound 32

Compound 32 was synthesized with a yield of 72% in the same manner as Compound 3, except that Intermediate 4 was used instead of 9,9'-dimethyl-2-bromofluorene. This compound was identified using HR-MS and NMR. C$_{54}$H$_{40}$N$_4$ calc.: 744.3253. found: 744.3253; $^1$H NMR (CDCl$_3$, 400 MHz) δ (ppm) 8.11 (d, 4H), 7.82 (d, 2H), 7.77 (s, 2H), 7.71 (d, 4H), 7.37-7.20 (m, 16H), 2.29 (s, 6H), 2.22 (s, 6H)

Synthesis Example 4

Synthesis of Compound 33

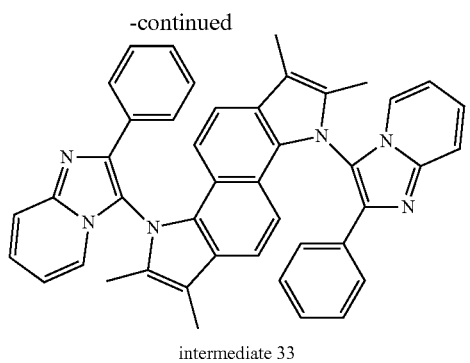

intermediate 33

Synthesis of Intermediate 5

3.98 g (20 mmol) of bromoacetophenone was dissolved in 100 mL of dimethoxyethane, and 2.0 g (20 mmol) of 2-aminopyridine was added thereto. The mixture was subjected to reaction at room temperature for 5 hours, and then stirred at 120° C. for 12 hours. After the reaction was completed, the mixture was cooled to room temperature. The solvent was removed, and 100 ml of dichloromethane was added thereto. The pH of the mixture was adjusted to 10 by adding a 10% sodium bicarbonate solution, and then the mixture was subjected to extraction using 100 mL of dichloromethane. An organic layer was collected and dried using magnesium sulfate to evaporate the solvent. The residue was separated and purified using silica gel column chromatography to obtain 2.4 g (yield: 65%) of Compound 5. This compound was identified using HR-MS. $C_{13}H_{10}N_2$ calc.: 194.0844. found: 194.0845

Synthesis of Intermediate 6

2.52 g (13 mmol) of Intermediate 5 was dissolved in 50 mL of pyridine, and 4.95 g (19.5 mmol) of iodine was added thereto. The mixture was stirred at 50° C. for 5 hours, and then an oxalic acid solution was added thereto to terminate the reaction. The mixture was subjected to extraction using 50 mL of dichloromethane, and an organic layer was collected and dried using magnesium sulfate to evaporate the solvent. The residue was separated and purified using silica gel column chromatography to obtain 3 g (yield: 72%) of Intermediate 6. This compound was identified using HR-MS. $C_{13}H_{91}N_2$ calc.: 319.9810. found: 319.9814

Synthesis of Compound 33

Compound 33 was synthesized with a yield of 64% in the same manner as Compound 3, except that Intermediate 6 was used instead of 9,9'-dimethyl-2-bromofluorene. This compound was identified using HR-MS and NMR. $C_{44}H_{34}N_6$ calc.: 646.2845. found: 646.28457; $^1$H NMR (CDCl$_3$, 400 MHz) δ (ppm) 8.88 (d, 2H), 7.88 (d, 2H), 7.85 (s, 2H), 7.80 (d, 2H), 7.48-7.26 (m, 10H), 7.25 (d, 2H), 6.90 (t, 2H), 2.33 (s, 6H), 2.29 (s, 6H)

Example 1

An anode was prepared by cutting a Corning 15 Ωcm$^2$ (1200 Å) ITO glass substrate to a size of 50 mm×50 mm×0.7 mm, ultrasonically cleaning the glass substrate using isopropyl alcohol and pure water for 5 minutes each, and then irradiating with UV light for 30 minutes and exposing to ozone to clean. Then, the anode was mounted in a vacuum deposition apparatus.

First, 2-TNATA as an HIL material was vacuum-deposited on the glass substrate to form a HIL having a thickness of 600 Å. Then, 4,4'-bis[N-(1-naphthyl)-N-phenylamino]biphenyl (NPB) as a hole transport compound was vacuum deposited on the HIL to form a HTL having a thickness of 300 Å.

Then, a green fluorescent host (Alq$_3$) and a green fluorescent dopant (C545T) were deposited simultaneously at a weight ratio of 98:2 on the HTL to form an EML with a thickness of 300 Å.

Then, Compound 3 was deposited on the EML to form an ETL having a thickness of 300 Å. Then LiF (a halogenated alkali metal) was deposited on the ETL to form an EIL having a thickness of 10 Å. Then, Al was deposited on the EIL to a thickness of 3000 Å (cathode), thereby forming a LiF/Al electrode. As a result, the manufacture of an organic light-emitting device was completed.

The organic light-emitting device had a driving voltage of 6.48 V at a current density of 50 mA/cm$^2$, a high emission brightness of 7,847 cd/m$^2$, color coordinates of (0.311, 0.642), and an emission efficiency of 15.69 cd/A.

Example 2

An organic light-emitting device was manufactured as in Example 1, except that Compound 12 was used instead of Compound 3 to form the ETL.

The organic light-emitting device had a driving voltage of 6.25 V at a current density of 50 mA/cm$^2$, a high emission brightness of 7,264 cd/m$^2$, color coordinates of (0.310, 0.642), and an emission efficiency of 14.53 cd/A.

Example 3

An organic light-emitting device was manufactured as in Example 1, except that Compound 32 was used instead of Compound 3 to form the ETL.

The organic light-emitting device had a driving voltage of 6.37 V at a current density of 50 mA/cm$^2$, a high emission brightness of 7,598 cd/m$^2$, color coordinates of (0.309, 0.643), and an emission efficiency of 15.20 cd/A.

Example 4

An organic light-emitting device was manufactured as in Example 1, except that Compound 33 was used instead of Compound 3 to form the ETL.

The organic light-emitting device had a driving voltage of 5.92 V at a current density of 50 mA/cm$^2$, a high emission brightness of 7,982 cd/m$^2$, color coordinates of (0.309, 0.642), and an emission efficiency of 15.96 cd/A.

Comparative Example 1

An organic light-emitting device was manufactured as in Example 1, except that Alq$_3$ was used instead of Compound 3 to form the ETL.

The organic light-emitting device had a driving voltage of 7.45 V at a current density of 50 mA/cm$^2$, a high emission brightness of 6,102 cd/m$^2$, color coordinates of (0.309, 0.642), and an emission efficiency of 12.2 cd/A.

The organic light-emitting devices manufactured using the heterocyclic compounds of Formula 1 according to the present invention had driving voltages that were lower by 1V or greater than when Alq$_3$ was used, and thus had higher efficiency and good I-V-L characteristics. In particular, lifetime characteristics were markedly improved by 100% or greater in the organic light-emitting devices according to Examples 1 through 4 as compared with the organic light-emitting device according to Comparative Example 1. The results are shown in Table 1 below.

TABLE 1

|  | Electron transporting material | Driving voltage | Current density | Brightness | Efficiency (cd/A) | Color coordinates | Half-life span (hr @ 100 mA/cm$^2$) |
|---|---|---|---|---|---|---|---|
| Example 1 | Compound 3 | 6.48 | 50 | 7,847 | 15.69 | (0.311, 0.642) | 452 hr |
| Example 2 | Compound 12 | 6.25 | 50 | 7,264 | 14.53 | (0.310, 0.642) | 380 hr |
| Example 3 | Compound 32 | 6.37 | 50 | 7,598 | 15.20 | (0.309, 0.643) | 460 hr |
| Example 4 | Compound 33 | 5.92 | 50 | 7,982 | 15.96 | (0.309, 0.642) | 493 hr |
| Comparative Example 1 | Alq$_3$ | 7.45 | 50 | 6,102 | 12.2 | (0.309, 0.642) | 237 hr |

The heterocyclic compounds according to embodiments of the present invention have good electrical characteristics, high charge transporting capabilities, light-emission capabilities, high glass transition temperatures ($T_g$), and crystallization prevention characteristics. Thus, the inventive heterocyclic compounds may be used as an electron transporting material for all-color fluorescent and phosphorescent devices, such as red, green, blue, and white fluorescent and phosphorescent devices, or as an emitting material for green, blue, and white fluorescent and phosphorescent devices. Thus, an organic light-emitting device with high-efficiency, low driving voltage, high luminance and long lifespan may be manufactured using the heterocylic compounds.

While the present invention has been illustrated and described with reference to certain exemplary embodiments, it is understood by those of ordinary skill in the art that various modifications and changes may be made to the described embodiments without departing from the spirit and scope of the present invention as defined by the following claims.

What is claimed is:

1. A heterocyclic compound comprising a compound represented by Formula 1 below:

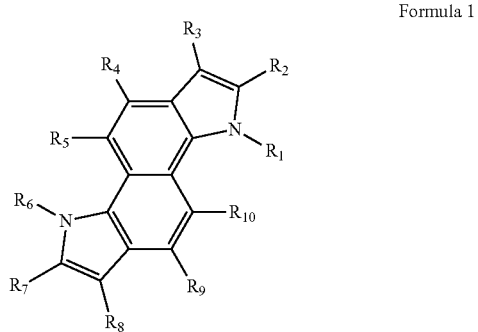

Formula 1 wherein:
each of $R_1$ through $R_{10}$ is independently selected from the group consisting of hydrogen atoms, heavy hydrogen atoms, substituted and unsubstituted $C_1$-$C_{50}$ alkyl groups, substituted and unsubstituted $C_3$-$C_{50}$ cycloalkyl groups, substituted and unsubstituted $C_1$-$C_{50}$ alkoxy groups, substituted and unsubstituted $C_5$-$C_{50}$ aryloxy groups, substituted and unsubstituted $C_5$-$C_{50}$ arylthio groups, substituted and unsubstituted $C_5$-$C_{60}$ aryl groups, amino groups substituted with at least one $R_5$-$R_{60}$ aryl group, substituted and unsubstituted $C_4$-$C_{60}$ heteroaryl groups, substituted and unsubstituted $C_6$-$C_{60}$ condensed polycyclic groups, halogen atoms, cyano groups, nitro groups, hydroxyl groups, and carboxyl groups, wherein two or more neighboring substituents selected from $R_1$ through $R_{10}$ may optionally combine to form an aromatic ring; and at least one of $R_1$ and $R_6$ is selected from the group consisting of:
unsubstituted monocyclic to tetracyclic aryl groups selected from the group consisting of phenyl groups, naphthyl groups, biphenyl groups, terphenyl groups, anthracenyl groups, fluorenyl groups, carbazolyl groups, and pyrene groups;
unsubstituted $C_4$-$C_{60}$ heteroaryl groups;
unsubstituted $C_5$-$C_{50}$ arylamine group;
substituted monocyclic to tetracyclic aryl groups selected from the group consisting of phenyl groups, naphthyl groups, biphenyl groups, terphenyl groups, anthracenyl groups, fluorenyl groups, carbazolyl groups, and pyrene groups substituted with a substituent selected from the group consisting of heavy hydrogen atoms, $C_1$-$C_5$ alkyl groups, $C_1$-$C_5$ alkoxy groups, cyano groups, amine groups, phenoxy groups, phenyl groups and halogen groups;
$C_4$-$C_{60}$ heteroaryl groups substituted with at least one substituent selected from the group consisting of heavy hydrogen atoms, $C_1$-$C_5$ alkyl groups, $C_1$-$C_5$ alkoxy groups, cyano groups, amine groups, phenoxy groups, phenyl groups, halogen groups and $C_5$-$C_{10}$ heteroaryl groups; and
$C_5$-$C_{50}$ arylamine groups substituted with at least one substituent selected from the group consisting of heavy hydrogen atoms, $C_1$-$C_5$ alkyl groups, $C_1$-$C_5$ alkoxy groups, cyano groups, amine groups, phenoxy groups, phenyl groups and halogen groups.

2. The heterocyclic compound of claim 1, wherein $R_1$ and $R_6$ are the same, or $R_2$ and $R_7$ are the same, or $R_3$ and $R_8$ are the same, or $R_4$ and $R_9$ are the same, or $R_5$ and $R_{10}$ are the same.

3. The heterocyclic compound of claim 1, wherein each of $R_2$, $R_3$, $R_7$ and $R_8$ is independently selected from the group consisting of methyl groups and phenyl groups.

4. The heterocyclic compound of claim 1, wherein the compound represented by Formula 1 comprises a compound selected from the group consisting of Compounds 3, 12, 32 and 33:

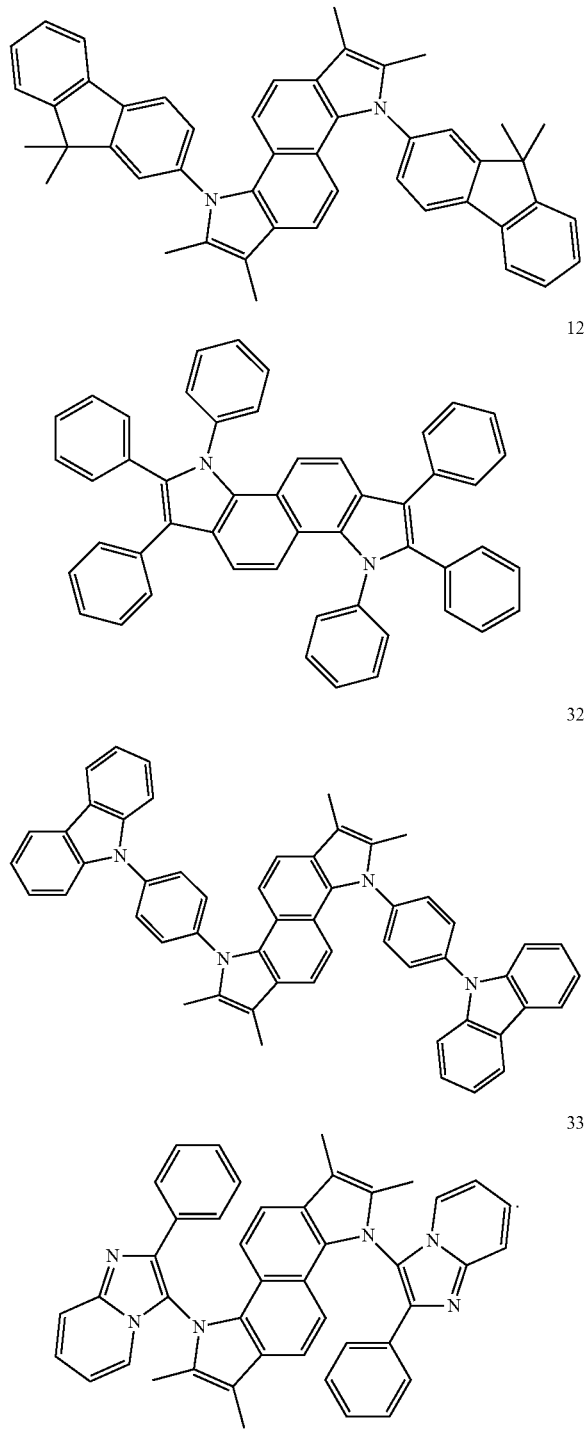

5. An organic light-emitting device comprising:
a first electrode;
a second electrode; and
at least one organic layer between the first electrode and the second electrode,
wherein the at least one organic layer comprises at least one layer comprising the heterocyclic compound of claim 1.

6. The organic light-emitting device of claim 5, wherein the at least one organic layer comprises an electron injection layer or an electron transport layer.

7. The organic light-emitting device of claim 5, wherein the at least one organic layer comprises a single layer having both electron injection and electron transport capabilities.

8. The organic light-emitting device of claim 5, wherein the at least one organic layer comprises an emission layer.

9. The organic light-emitting device of claim 5, wherein the at least one organic layer comprises an emission layer, and the heterocylic compound is a host for a fluorescent or phosphorescent device.

10. The organic light-emitting device of claim 5, wherein the at least one organic layer comprises an emission layer, and the heterocyclic compound is a fluorescent dopant.

11. The organic light-emitting device of claim 5, wherein the at least one organic layer comprises an emission layer, and an electron injection layer or an electron transport layer, wherein the emission layer comprises an anthracene compound or an arylamine compound or a styryl compound.

12. The organic light-emitting device of claim 5, wherein the at least one organic layer comprises an emission layer, and an electron injection layer or an electron transport layer, wherein the emission layer comprises a red emission layer, a green emission layer, a blue emission layer or a white emission layer that comprises a phosphorescent compound.

13. The organic light-emitting device of claim 5, wherein the at least one organic layer comprises at least one layer selected from the group consisting of a hole injection layer, a hole transport layer, an electron blocking layer, an emission layer, a hole blocking layer, an electron transport layer, and an electron injection layer.

14. The organic light-emitting device of claim 13, wherein the organic light-emitting device has a first electrode/hole injection layer/emission layer/second electrode structure, or a first electrode/hole injection layer/hole transport layer/emission layer/electron transport layer/second electrode structure, or a first electrode/hole injection layer/hole transport layer/emission layer/electron transport layer/electron injection layer/second electrode layer structure.

15. A flat panel display device comprising the organic light-emitting device of claim 5, wherein the first electrode of the organic light-emitting device is electrically connected to a source electrode or a drain electrode of a thin-film transistor.

16. An organic light-emitting device comprising:
a first electrode;
a second electrode; and
an organic layer between the first electrode and the second electrode, wherein the organic layer comprises at least one layer comprising the heterocyclic compound of claim 1, the at least one layer being formed using a wet process.

* * * * *